US012702567B2

(12) United States Patent
Sinha et al.

(10) Patent No.: US 12,702,567 B2
(45) Date of Patent: Aug. 11, 2026

(54) IMPLANTABLE CAGES AND PLATES HAVING ALIGNMENT MARKINGS AND RELATED METHODS OF USING THE SAME

(71) Applicant: INTELIVATION TECHNOLOGIES LLC, Saint Simons Island, GA (US)

(72) Inventors: Amit Sinha, Saint Simons Island, GA (US); David Rathbun, Saint Simons Island, GA (US); Rob Anderson, Saint Simons Island, GA (US)

(73) Assignee: INTELIVATION TECHNOLOGIES LLC, Saint Simons Island, GA (US)

( * ) Notice: Subject to any disclaimer, the term of this patent is extended or adjusted under 35 U.S.C. 154(b) by 0 days.

(21) Appl. No.: 18/843,888

(22) PCT Filed: Mar. 3, 2023

(86) PCT No.: PCT/US2023/063673
§ 371 (c)(1),
(2) Date: Sep. 4, 2024

(87) PCT Pub. No.: WO2023/168398
PCT Pub. Date: Sep. 7, 2023

(65) Prior Publication Data

US 2025/0177163 A1 Jun. 5, 2025

Related U.S. Application Data

(60) Provisional application No. 63/316,752, filed on Mar. 4, 2022.

(51) Int. Cl.
*A61B 17/70* (2006.01)
*A61F 2/44* (2006.01)
(Continued)

(52) U.S. Cl.
CPC ........ *A61F 2/4455* (2013.01); *A61B 17/7059* (2013.01); *A61B 2017/564* (2013.01);
(Continued)

(58) Field of Classification Search
CPC .......... A61F 2/44; A61F 2/4455; A61F 2/447; A61F 2/4611; A61F 2/30; A61B 17/8042;
(Continued)

(56) References Cited

U.S. PATENT DOCUMENTS 6,074,423 A * 6/2000 Lawson .................. A61F 2/446 606/279
6,096,081 A * 8/2000 Grivas ............... A61B 17/1671 623/901
(Continued)

OTHER PUBLICATIONS

International Preliminary Report on Patentability date Sep. 19, 2024.
(Continued)

*Primary Examiner* — Jessica Weiss
(74) *Attorney, Agent, or Firm* — Meunier Carlin & Curfman LLC

(57) ABSTRACT

An implantable construct for stabilizing a first bone structure and a second bone structure of a patient may include a cage configured for positioning between the first bone structure and the second bone structure, and a plate configured for positioning over the cage and being secured to each of the first bone structure and the second bone structure. The cage may include one or more cage alignment markings disposed on an exterior surface of the cage. The plate may include one or more plate alignment markings disposed on an exterior surface of the plate and configured for being aligned with the one or more cage alignment markings such that the plate is aligned with the cage.

23 Claims, 14 Drawing Sheets

(51) Int. Cl.

| | |
|---|---|
| *A61B 17/56* | (2006.01) |
| *A61B 90/00* | (2016.01) |
| *A61F 2/30* | (2006.01) |

(52) U.S. Cl.

CPC ................. *A61B 2090/0808* (2016.02); *A61B 2090/3937* (2016.02); *A61F 2002/30617* (2013.01)

(58) Field of Classification Search

CPC ..... A61B 17/7059; A61B 17/70; A61B 17/56; A61B 90/00; A61B 2017/564; A61B 2090/0807; A61B 2090/0808; A61B 2090/3937

USPC ............................... 623/17.11–17.16; 606/99

See application file for complete search history.

(56) References Cited

U.S. PATENT DOCUMENTS

| | | | | |
|---|---|---|---|---|
| 6,156,037 | A | 12/2000 | LeHuec et al. | |
| 6,241,771 | B1 | 6/2001 | Gresser et al. | |
| 6,482,233 | B1 | 11/2002 | Aebi et al. | |
| 6,676,703 | B2 | 1/2004 | Biscup | |
| 7,637,950 | B2 | 12/2009 | Baccelli et al. | |
| D619,255 | S | 7/2010 | Richter et al. | |
| 8,267,997 | B2 | 9/2012 | Colleran | |
| D708,747 | S | 7/2014 | Curran et al. | |
| 8,840,667 | B1* | 9/2014 | Tumialan | A61B 17/1728 623/17.11 |
| D735,859 | S | 8/2015 | Palinchik et al. | |
| D742,008 | S | 10/2015 | Schifano et al. | |
| 9,358,122 | B2 | 6/2016 | Soo | |
| 9,474,624 | B1 | 10/2016 | Ahn | |
| D790,704 | S | 6/2017 | Yang | |
| 10,045,860 | B2 | 8/2018 | Berry et al. | |
| D835,788 | S | 12/2018 | Jones et al. | |
| 2002/0128712 | A1* | 9/2002 | Michelson | A61F 2/446 606/301 |
| 2005/0065606 | A1 | 3/2005 | Jackson | |
| 2005/0143822 | A1 | 6/2005 | Paul | |
| 2006/0100705 | A1 | 5/2006 | Puno et al. | |
| 2007/0100452 | A1 | 5/2007 | Prosser | |
| 2010/0168798 | A1 | 7/2010 | Clineff et al. | |
| 2012/0078371 | A1 | 3/2012 | Gamache et al. | |
| 2012/0239151 | A1 | 9/2012 | Ulrich, Jr. et al. | |
| 2013/0006363 | A1 | 1/2013 | Ullrich, Jr. et al. | |
| 2014/0094856 | A1 | 4/2014 | Sinha | |
| 2014/0128979 | A1* | 5/2014 | Womble | A61B 17/70 623/17.16 |
| 2017/0020685 | A1* | 1/2017 | Geisler | A61F 2/30965 |
| 2017/0156882 | A1* | 6/2017 | Rathbun | A61F 2/447 |
| 2017/0156884 | A1 | 6/2017 | Rathbun et al. | |
| 2020/0113699 | A1* | 4/2020 | Altarac | A61F 2/447 |
| 2020/0352723 | A1 | 11/2020 | Jimenez et al. | |
| 2020/0352739 | A1* | 11/2020 | Ouidja | A61F 2/30749 |
| 2020/0375635 | A1* | 12/2020 | Bohl | A61B 17/7064 |
| 2021/0401585 | A1 | 12/2021 | Suh et al. | |
| 2023/0263639 | A1 | 8/2023 | Zhang et al. | |

OTHER PUBLICATIONS

ISA/US, International Search Report & Written Opinion of International Searching Authority for PCT/US2023/063673, mailed Sep. 27, 2023, 9 pages.

* cited by examiner 210
214
232
216
226
224
242a
242f
222
242c
238
212
242d
218
242e
236
242b
234

$W_c$
210
216
226
242a
222
234
242d
224
$H_c$
242e
242f
236
242c
238
242b
212
218
228

210
232
216
226
224
222
214
218
228

IMPLANTABLE CAGES AND PLATES HAVING ALIGNMENT MARKINGS AND RELATED METHODS OF USING THE SAME

CROSS REFERENCE TO RELATED APPLICATIONS

This application is a U.S. National Stage application filed under 35 U.S.C. § 371 of PCT/US2023/063673, filed Mar. 3, 2023, which claims the benefit of U.S. Provisional Patent Application No. 63/316,752, filed Mar. 4, 2022, the contents of which are incorporated herein by reference in their entirety.

FIELD OF THE DISCLOSURE

The present disclosure relates generally to implantable medical devices and more particularly to implantable cages and plates having alignment markings and related methods of using the same.

BACKGROUND OF THE DISCLOSURE

In various types of surgical procedures, a cage and a plate may be implanted in a patient as part of a construct for stabilizing bone structures of the patient. For example, a cage may be positioned between a first bone structure and a second bone structure, and a plate may be positioned over the cage and then secured to each of the first bone structure and the second bone structure by screws or other types of mechanical fasteners. In some instances, the construct may stabilize the first bone structure and the second bone structure to facilitate bony fusion therebetween. Positioning of a cage and a plate overlying the cage often may be implemented in spinal procedures, although other types of surgical procedures performed with respect to other portions of the body also may utilize a cage and a plate arranged in a similar manner. In some instances, when a surgeon positions the plate over the cage, it may be challenging for the surgeon to visualize how the plate is oriented relative to the cage. For example, blood or tissue at the surgical site may obstruct direct visualization of the cage or the plate and/or the cage or the plate may be formed of materials that are not readily discernable using medical imaging during the procedure. As a result, the plate may be implanted at an orientation that is slanted relative to the cage, which may be apparent on a post-operative X-ray image. In many instances, the slanted orientation of the plate may be clinically irrelevant, as the construct still may provide desired stabilization of the relevant bone structures. However, the surgeon generally may prefer to avoid implanting the plate at a slanted orientation relative to the cage.

A need therefore exists for improved implantable cages and plates and related methods of using the same, which may overcome one or more of the above-mentioned challenges associated with existing cages and plates and their use.

SUMMARY OF THE DISCLOSURE

The present disclosure provides implantable cages and plates having alignment markings and related methods of using the same to align a cage and a plate during a surgical procedure.

In one aspect, an implantable construct for stabilizing a first bone structure and a second bone structure of a patient is provided. In one embodiment, the implantable construct may include a cage configured for positioning between the first bone structure and the second bone structure, and a plate configured for positioning over the cage and being secured to each of the first bone structure and the second bone structure. The cage may include one or more cage alignment markings disposed on an exterior surface of the cage. The plate may include one or more plate alignment markings disposed on an exterior surface of the plate and configured for being aligned with the one or more cage alignment markings such that the plate is aligned with the cage.

In some embodiments, the one or more cage alignment markings may include one or more cage alignment lines, and the one or more plate alignment markings may include one or more plate alignment lines. In some embodiments, the cage may have a height and a width extending perpendicular to the height of the cage, the one or more cage alignment markings may include one or more cage alignment lines extending in a direction of the height of the cage, the plate may have a length and a width extending perpendicular to the length of the plate, and the one or more plate alignment markings may include one or more plate alignment lines extending in a direction of the length of the plate. In some embodiments, the one or more plate alignment lines may be configured for being aligned with the one or more cage alignment lines in the direction of the height of the cage such that the plate is aligned with the cage. In some embodiments, the one or more cage alignment lines may include a first cage alignment line and a second cage alignment line, and the one or more plate alignment lines may include a first plate alignment line and a second plate alignment line. In some embodiments, the first cage alignment line and the second cage alignment line may be aligned with one another in the direction of the height of the cage, and the first plate alignment line and the second plate alignment line may be aligned with one another in the direction of the length of the plate. In some embodiments, the first cage alignment line and the second cage alignment line may be centered on the exterior surface of the cage in a direction of the width of the cage, and the first plate alignment line and the second plate alignment line may be centered on the exterior surface of the plate in a direction of the width of the plate. In some embodiments, the cage may include a cage opening defined in the exterior surface of the cage and disposed between the first cage alignment line and the second cage alignment line in the direction of the height of the cage, and the plate may include a plate opening defined in the exterior surface of the plate and disposed between the first plate alignment line and the second plate alignment line in the direction of the length of the plate. In some embodiments, the first cage alignment line and the second cage alignment line may be spaced apart from one another in a direction of the width of the cage, and the first plate alignment line and the second plate alignment line may be spaced apart from one another in a direction of the width of the plate. In some embodiments, the one or more cage alignment lines also may include a third cage alignment line and a fourth cage alignment line spaced apart from one another in the direction of the width of the cage, and the one or more plate alignment lines also may include a third plate alignment line and a fourth plate alignment line spaced apart from one another in the direction of the width of the plate. In some embodiments, the first cage alignment line and the third cage alignment line may be aligned with one another in the direction of the height of the cage, the second cage alignment line and the fourth cage alignment line may be aligned with one another in the direction of the height of the cage, the first plate alignment line and the third plate alignment line may be aligned with one another in the direction of the length of the plate, and the second plate alignment line and the fourth plate alignment line may be aligned with one another in the direction of the length of the plate.

In some embodiments, the cage may have a height and a width extending perpendicular to the height of the cage, the one or more cage alignment markings may include one or more cage alignment lines extending in a direction of the width of the cage, the plate may have a length and a width extending perpendicular to the length of the plate, and the one or more plate alignment markings may include one or more plate alignment lines extending in a direction of the width of the plate. In some embodiments, the one or more plate alignment lines may be configured for being aligned with the one or more cage alignment lines in the direction of the width of the cage such that the plate is aligned with the cage. In some embodiments, the one or more cage alignment lines may include a first cage alignment line and a second cage alignment line, and the one or more plate alignment lines may include a first plate alignment line and a second plate alignment line. In some embodiments, the first cage alignment line and the second cage alignment line may be aligned with one another in the direction of the width of the cage, and the first plate alignment line and the second plate alignment line may be aligned with one another in the direction of the width of the plate. In some embodiments, the first cage alignment line and the second cage alignment line my be centered on the exterior surface of the cage in a direction of the height of the cage, and the first plate alignment line and the second plate alignment line may be centered on the exterior surface of the plate in a direction of the length of the plate. In some embodiments, the cage may include a cage opening defined in the exterior surface of the cage and disposed between the first cage alignment line and the second cage alignment line in the direction of the width of the cage, and the plate may include a plate opening defined in the exterior surface of the plate and disposed between the first plate alignment line and the second plate alignment line in the direction of the width of the plate. In some embodiments, the first cage alignment line and the second cage alignment line may be spaced apart from one another in a direction of the height of the cage, and the first plate alignment line and the second plate alignment line may be spaced apart from one another in a direction of the length of the plate. In some embodiments, the one or more cage alignment lines also may include a third cage alignment line and a fourth cage alignment line spaced apart from one another in the direction of the height of the cage, and the one or more plate alignment lines also may include a third plate alignment line and a fourth plate alignment line spaced apart from one another in the direction of the length of the plate. In some embodiments, the first cage alignment line and the third cage alignment line may be aligned with one another in the direction of the width of the cage, the second cage alignment line and the fourth cage alignment line may be aligned with one another in the direction of the width of the cage, the first plate alignment line and the third plate alignment line may be aligned with one another in the direction of the width of the plate, and the second plate alignment line and the fourth plate alignment line may be aligned with one another in the direction of the width of the plate.

In some embodiments, the cage may have a height and a width extending perpendicular to the height of the cage, the one or more cage alignment markings may include a first cage alignment line extending in a direction of the height of the cage and a second cage alignment line extending in a direction of the width of the cage, the plate may have a length and a width extending perpendicular to the length of the plate, and the one or more plate alignment markings may include a first plate alignment line extending in a direction of the length of the cage and a second plate alignment line extending in a direction of the width of the plate. In some embodiments, the first plate alignment line may be configured for being aligned with the first cage alignment line in the direction of the height of the cage such that the plate is aligned with the cage, and the second plate alignment line may be configured for being aligned with the second cage alignment line in the direction of the width of the cage such that the plate is aligned with the cage. In some embodiments, the first cage alignment line may be centered on the exterior surface of the cage in the direction of the width of the cage, the second cage alignment line may be centered on the exterior surface of the cage in the direction of the width of the cage, the first plate alignment line may be centered on the exterior surface of the plate in the direction of the width of the plate, and the second plate alignment line may be centered on the exterior surface of the plate in the direction of the length of the plate. In some embodiments, the one or more cage alignment markings also may include a third cage alignment line extending in the direction of the height of the cage and a fourth cage alignment line extending in the direction of the width of the cage, and the one or more plate alignment markings also may include a third plate alignment line extending in the direction of the length of the cage and a fourth plate alignment line extending in the direction of the width of the plate. In some embodiments, the first cage alignment line and the third cage alignment line may be aligned with one another in the direction of the height of the cage, the second cage alignment line and the fourth cage alignment line may be aligned with one another in the direction of the width of the cage, the first plate alignment line and the third plate alignment line may be aligned with one another in the direction of the length of the plate, and the second plate alignment line and the fourth plate alignment line may be aligned with one another in the direction of the width of the plate. In some embodiments, the cage may include a cage opening defined in the exterior surface of the cage and disposed between the first cage alignment line and the third cage alignment line in the direction of the height of the cage and between the second cage alignment line and the fourth cage alignment line in the direction of the width of the cage, and the plate may include a plate opening defined in the exterior surface of the plate and disposed between the first plate alignment line and the third plate alignment line in the direction of the length of the plate and between the second plate alignment line and the fourth plate alignment line in the direction of the width of the plate.

In some embodiments, the cage may have a height and a width extending perpendicular to the height of the cage, the one or more cage alignment markings may include a first cage alignment line extending in a first direction transverse to each of the height and the width of the cage, the plate may have a length and a width extending perpendicular to the length of the plate, and the one or more plate alignment markings may include a first plate alignment line extending in a second direction transverse to each of the length and the width of the plate. In some embodiments, the first plate alignment line may be configured for being aligned with the first cage alignment line in the first direction such that the plate is aligned with the cage. In some embodiments, the one or more cage alignment markings also may include a second cage alignment line extending in a third direction transverse to each of the height and the width of the cage and transverse to the first direction, and the one or more plate alignment markings also may include a second plate alignment line extending in a fourth direction transverse to each of the length and the width of the plate and transverse to the second direction. In some embodiments, the second plate alignment line may be configured for being aligned with the second cage alignment line in the third direction such that the plate is aligned with the cage. In some embodiments, the one or more cage alignment markings also may include a third cage alignment line extending in a fifth direction transverse to each of the height and the width of the cage, transverse to the third direction, and parallel to the first direction, and a fourth cage alignment line extending in a sixth direction transverse to each of the height and the width of the cage, transverse to the first direction, and parallel to the third direction, and the one or more plate alignment markings also may include a third plate alignment line extending in a seventh direction transverse to each of the length and the width of the plate, transverse to the fourth direction, and parallel to the second direction, and a fourth plate alignment line extending in an eight direction transverse to each of the length and the width of the plate, transverse to the second direction, and parallel to the fourth direction. In some embodiments, the third plate alignment line may be configured for being aligned with the third cage alignment line in the fifth direction such that the plate is aligned with the cage, and the fourth plate alignment line may be configured for being aligned with the fourth cage alignment line in the sixth direction such that the plate is aligned with the cage.

In some embodiments, the one or more cage alignment markings may be laser markings disposed on the exterior surface of the cage, and the one or more plate alignment markings may be laser markings disposed on the exterior surface of the plate. In some embodiments, the one or more cage alignment markings may be laser etched markings disposed on the exterior surface of the cage, and the one or more plate alignment markings may be laser etched markings disposed on the exterior surface of the plate. In some embodiments, the one or more cage alignment markings may be laser engraved markings disposed on the exterior surface of the cage, and the one or more plate alignment markings may be laser engraved markings disposed on the exterior surface of the plate. In some embodiments, the implantable construct also may include a plurality of screws configured for securing the plate to each of the first bone structure and the second bone structure. In some embodiments, the first bone structure may be a first vertebra, and the second bone structure may be a second vertebra adjacent to the first vertebra. In some embodiments, the cage may be a spinal cage, and the plate may be a spinal plate. In some embodiments, the cage may be an anterior spinal cage, and the plate may be an anterior spinal plate. In some embodiments, the exterior surface of the cage may be an anterior surface of the cage, and the exterior surface of the plate may be an anterior surface of the plate.

In another aspect, a method of using an implantable construct for stabilizing a first bone structure and a second bone structure of a patient is provided. In one embodiment, the method may include positioning a cage of the implantable construct between the first bone structure and the second bone structure. The cage may include one or more cage alignment markings disposed on an exterior surface of the cage. The method also may include positioning a plate of the implantable construct over the cage. The plate may include one or more plate alignment markings disposed on an exterior surface of the plate. The method also may include aligning the one or more plate alignment markings with the one or more cage alignment markings such that the plate is aligned with the cage, and securing the plate to each of the first bone structure and the second bone structure.

In some embodiments, the one or more cage alignment markings may include one or more cage alignment lines, and the one or more plate alignment markings may include one or more plate alignment lines. In some embodiments, the cage may have a height and a width extending perpendicular to the height of the cage, the one or more cage alignment markings may include one or more cage alignment lines extending in a direction of the height of the cage, the plate may have a length and a width extending perpendicular to the length of the plate, and the one or more plate alignment markings may include one or more plate alignment lines extending in a direction of the length of the plate. In some embodiments, aligning the one or more plate alignment markings with the one or more cage alignment markings may include aligning the one or more plate alignment lines with the one or more cage alignment lines in the direction of the height of the cage such that the plate is aligned with the cage. In some embodiments, the one or more cage alignment lines may include a first cage alignment line and a second cage alignment line, and the one or more plate alignment lines may include a first plate alignment line and a second plate alignment line. In some embodiments, the first cage alignment line and the second cage alignment line may be aligned with one another in the direction of the height of the cage, and the first plate alignment line and the second plate alignment line may be aligned with one another in the direction of the length of the plate. In some embodiments, the first cage alignment line and the second cage alignment line may be centered on the exterior surface of the cage in a direction of the width of the cage, and the first plate alignment line and the second plate alignment line may be centered on the exterior surface of the plate in a direction of the width of the plate. In some embodiments, the cage may include a cage opening defined in the exterior surface of the cage and disposed between the first cage alignment line and the second cage alignment line in the direction of the height of the cage, and the plate may include a plate opening defined in the exterior surface of the plate and disposed between the first plate alignment line and the second plate alignment line in the direction of the length of the plate. In some embodiments, the first cage alignment line and the second cage alignment line may be spaced apart from one another in a direction of the width of the cage, and the first plate alignment line and the second plate alignment line may be spaced apart from one another in a direction of the width of the plate. In some embodiments, the one or more cage alignment lines also may include a third cage alignment line and a fourth cage alignment line spaced apart from one another in the direction of the width of the cage, and the one or more plate alignment lines also may include a third plate alignment line and a fourth plate alignment line spaced apart from one another in the direction of the width of the plate. In some embodiments, the first cage alignment line and the third cage alignment line may be aligned with one another in the direction of the height of the cage, the second cage alignment line and the fourth cage alignment line may be aligned with one another in the direction of the height of the cage, the first plate alignment line and the third plate alignment line may be aligned with one another in the direction of the length of the plate, and the second plate alignment line and the fourth plate alignment line may be aligned with one another in the direction of the length of the plate.

In some embodiments, the cage may have a height and a width extending perpendicular to the height of the cage, the one or more cage alignment markings may include one or more cage alignment lines extending in a direction of the width of the cage, the plate may have a length and a width extending perpendicular to the length of the plate, and the one or more plate alignment markings may include one or more plate alignment lines extending in a direction of the width of the plate. In some embodiments, aligning the one or more plate alignment markings with the one or more cage alignment markings may include aligning the one or more plate alignment lines with the one or more cage alignment lines in the direction of the width of the cage such that the plate is aligned with the cage. In some embodiments, the one or more cage alignment lines may include a first cage alignment line and a second cage alignment line, and the one or more plate alignment lines may include a first plate alignment line and a second plate alignment line. In some embodiments, the first cage alignment line and the second cage alignment line may be aligned with one another in the direction of the width of the cage, and the first plate alignment line and the second plate alignment line may be aligned with one another in the direction of the width of the plate. In some embodiments, the first cage alignment line and the second cage alignment line my be centered on the exterior surface of the cage in a direction of the height of the cage, and the first plate alignment line and the second plate alignment line may be centered on the exterior surface of the plate in a direction of the length of the plate. In some embodiments, the cage may include a cage opening defined in the exterior surface of the cage and disposed between the first cage alignment line and the second cage alignment line in the direction of the width of the cage, and the plate may include a plate opening defined in the exterior surface of the plate and disposed between the first plate alignment line and the second plate alignment line in the direction of the width of the plate. In some embodiments, the first cage alignment line and the second cage alignment line may be spaced apart from one another in a direction of the height of the cage, and the first plate alignment line and the second plate alignment line may be spaced apart from one another in a direction of the length of the plate. In some embodiments, the one or more cage alignment lines also may include a third cage alignment line and a fourth cage alignment line spaced apart from one another in the direction of the height of the cage, and the one or more plate alignment lines also may include a third plate alignment line and a fourth plate alignment line spaced apart from one another in the direction of the length of the plate. In some embodiments, the first cage alignment line and the third cage alignment line may be aligned with one another in the direction of the width of the cage, the second cage alignment line and the fourth cage alignment line may be aligned with one another in the direction of the width of the cage, the first plate alignment line and the third plate alignment line may be aligned with one another in the direction of the width of the plate, and the second plate alignment line and the fourth plate alignment line may be aligned with one another in the direction of the width of the plate.

In some embodiments, the cage may have a height and a width extending perpendicular to the height of the cage, the one or more cage alignment markings may include a first cage alignment line extending in a direction of the height of the cage and a second cage alignment line extending in a direction of the width of the cage, the plate may have a length and a width extending perpendicular to the length of the plate, and the one or more plate alignment markings may include a first plate alignment line extending in a direction of the length of the cage and a second plate alignment line extending in a direction of the width of the plate. In some embodiments, aligning the one or more plate alignment markings with the one or more cage alignment markings may include aligning the first plate alignment line with the first cage alignment line in the direction of the height of the cage such that the plate is aligned with the cage, and aligning the second plate alignment line with the second cage alignment line in the direction of the width of the cage such that the plate is aligned with the cage. In some embodiments, the first cage alignment line may be centered on the exterior surface of the cage in the direction of the width of the cage, the second cage alignment line may be centered on the exterior surface of the cage in the direction of the width of the cage, the first plate alignment line may be centered on the exterior surface of the plate in the direction of the width of the plate, and the second plate alignment line may be centered on the exterior surface of the plate in the direction of the length of the plate. In some embodiments, the one or more cage alignment markings also may include a third cage alignment line extending in the direction of the height of the cage and a fourth cage alignment line extending in the direction of the width of the cage, and the one or more plate alignment markings also may include a third plate alignment line extending in the direction of the length of the cage and a fourth plate alignment line extending in the direction of the width of the plate. In some embodiments, the first cage alignment line and the third cage alignment line may be aligned with one another in the direction of the height of the cage, the second cage alignment line and the fourth cage alignment line may be aligned with one another in the direction of the width of the cage, the first plate alignment line and the third plate alignment line may be aligned with one another in the direction of the length of the plate, and the second plate alignment line and the fourth plate alignment line may be aligned with one another in the direction of the width of the plate. In some embodiments, the cage may include a cage opening defined in the exterior surface of the cage and disposed between the first cage alignment line and the third cage alignment line in the direction of the height of the cage and between the second cage alignment line and the fourth cage alignment line in the direction of the width of the cage, and the plate may include a plate opening defined in the exterior surface of the plate and disposed between the first plate alignment line and the third plate alignment line in the direction of the length of the plate and between the second plate alignment line and the fourth plate alignment line in the direction of the width of the plate.

In some embodiments, the cage may have a height and a width extending perpendicular to the height of the cage, the one or more cage alignment markings may include a first cage alignment line extending in a first direction transverse to each of the height and the width of the cage, the plate may have a length and a width extending perpendicular to the length of the plate, and the one or more plate alignment markings may include a first plate alignment line extending in a second direction transverse to each of the length and the width of the plate. In some embodiments, aligning the one or more plate alignment markings with the one or more cage alignment markings may include aligning the first plate alignment line with the first cage alignment line in the first direction such that the plate is aligned with the cage. In some embodiments, the one or more cage alignment markings also may include a second cage alignment line extending in a third direction transverse to each of the height and the width of the cage and transverse to the first direction, and the one or more plate alignment markings also may include a second plate alignment line extending in a fourth direction transverse to each of the length and the width of the plate and transverse to the second direction. In some embodiments, aligning the one or more plate alignment markings with the one or more cage alignment markings may include aligning the second plate alignment line with the second cage alignment line in the third direction such that the plate is aligned with the cage. In some embodiments, the one or more cage alignment markings also may include a third cage alignment line extending in a fifth direction transverse to each of the height and the width of the cage, transverse to the third direction, and parallel to the first direction, and a fourth cage alignment line extending in a sixth direction transverse to each of the height and the width of the cage, transverse to the first direction, and parallel to the third direction, and the one or more plate alignment markings also may include a third plate alignment line extending in a seventh direction transverse to each of the length and the width of the plate, transverse to the fourth direction, and parallel to the second direction, and a fourth plate alignment line extending in an eight direction transverse to each of the length and the width of the plate, transverse to the second direction, and parallel to the fourth direction. In some embodiments, aligning the one or more plate alignment markings with the one or more cage alignment markings may include aligning the third plate alignment line with the third cage alignment line in the fifth direction such that the plate is aligned with the cage, and aligning the fourth plate alignment line with the fourth cage alignment line in the sixth direction such that the plate is aligned with the cage.

In some embodiments, the one or more cage alignment markings may be laser markings disposed on the exterior surface of the cage, and the one or more plate alignment markings may be laser markings disposed on the exterior surface of the plate. In some embodiments, the one or more cage alignment markings may be laser etched markings disposed on the exterior surface of the cage, and the one or more plate alignment markings may be laser etched markings disposed on the exterior surface of the plate. In some embodiments, the one or more cage alignment markings may be laser engraved markings disposed on the exterior surface of the cage, and the one or more plate alignment markings may be laser engraved markings disposed on the exterior surface of the plate. In some embodiments, securing the plate to each of the first bone structure and the second bone structure may include securing the plate to each of the first bone structure and the second bone structure using a plurality of screws of the implantable construct. In some embodiments, the first bone structure may be a first vertebra, and the second bone structure may be a second vertebra adjacent to the first vertebra. In some embodiments, the cage may be a spinal cage, and the plate may be a spinal plate. In some embodiments, the cage may be an anterior spinal cage, and the plate may be an anterior spinal plate. In some embodiments, the exterior surface of the cage may be an anterior surface of the cage, and the exterior surface of the plate may be an anterior surface of the plate.

These and other aspects and improvements of the present disclosure will become apparent to one of ordinary skill in the art upon review of the following detailed description when taken in conjunction with the several drawings and the appended claims.

Figures 1A, 1B:
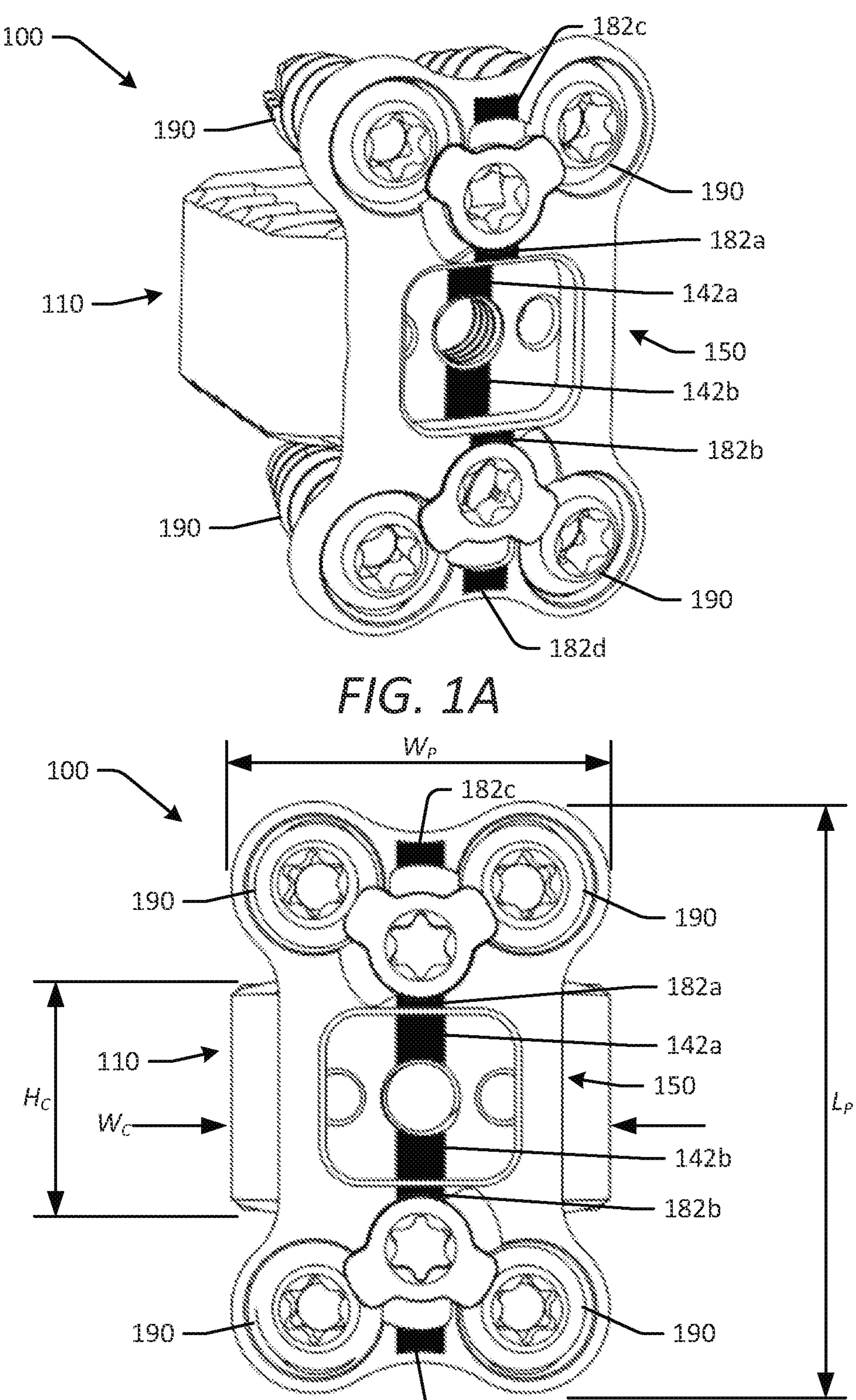
FIG. 1A is a perspective view of an example implantable construct in accordance with embodiments of the disclosure, showing a cage, a plate, and screws of the implantable construct.
FIG. 1B is a front view of the implantable construct of FIG. 1A.
Figure 1C:
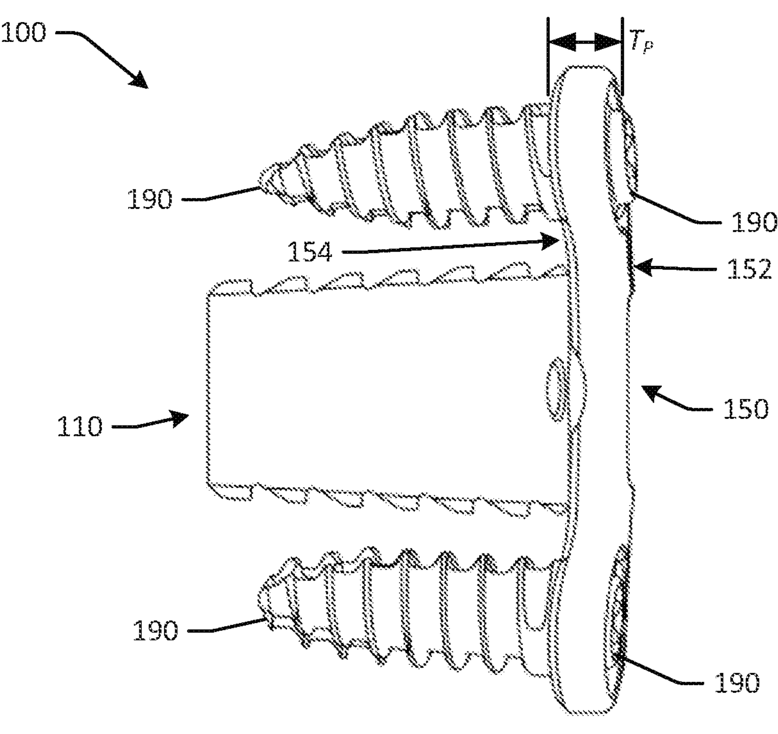
FIG. 1C is a side view of the implantable construct of FIG. 1A.
Figure 1D:
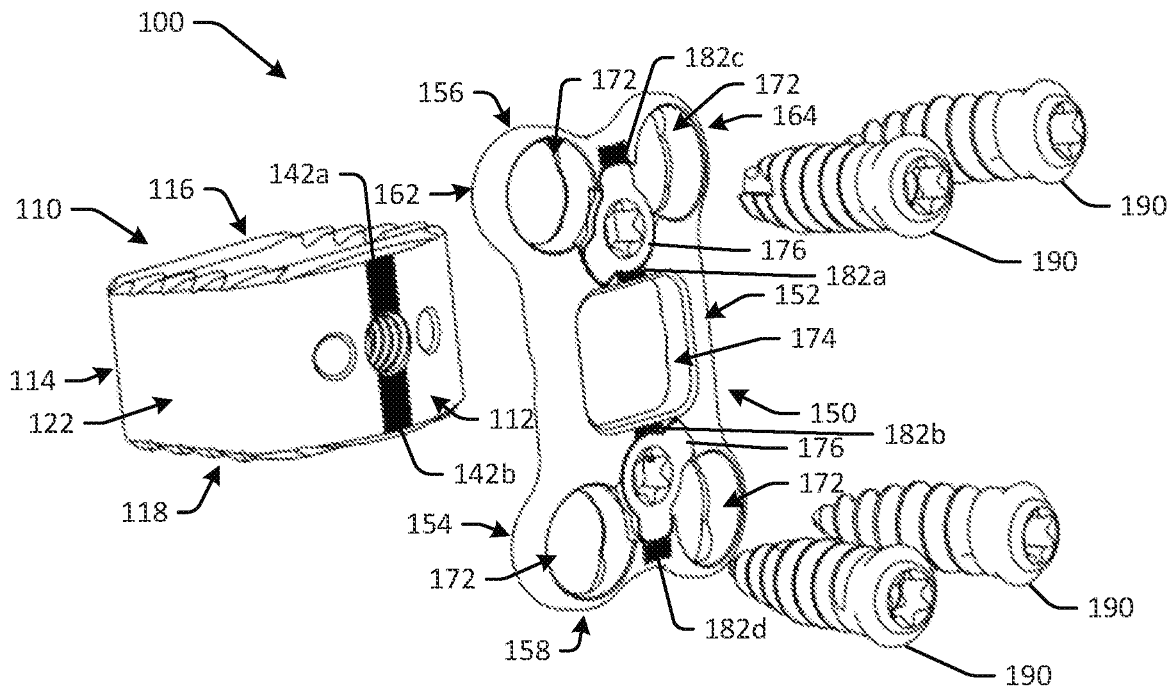
FIG. 1D is an exploded perspective view of the implantable construct of FIG. 1A.
Figures 1E, 1F, 1G:
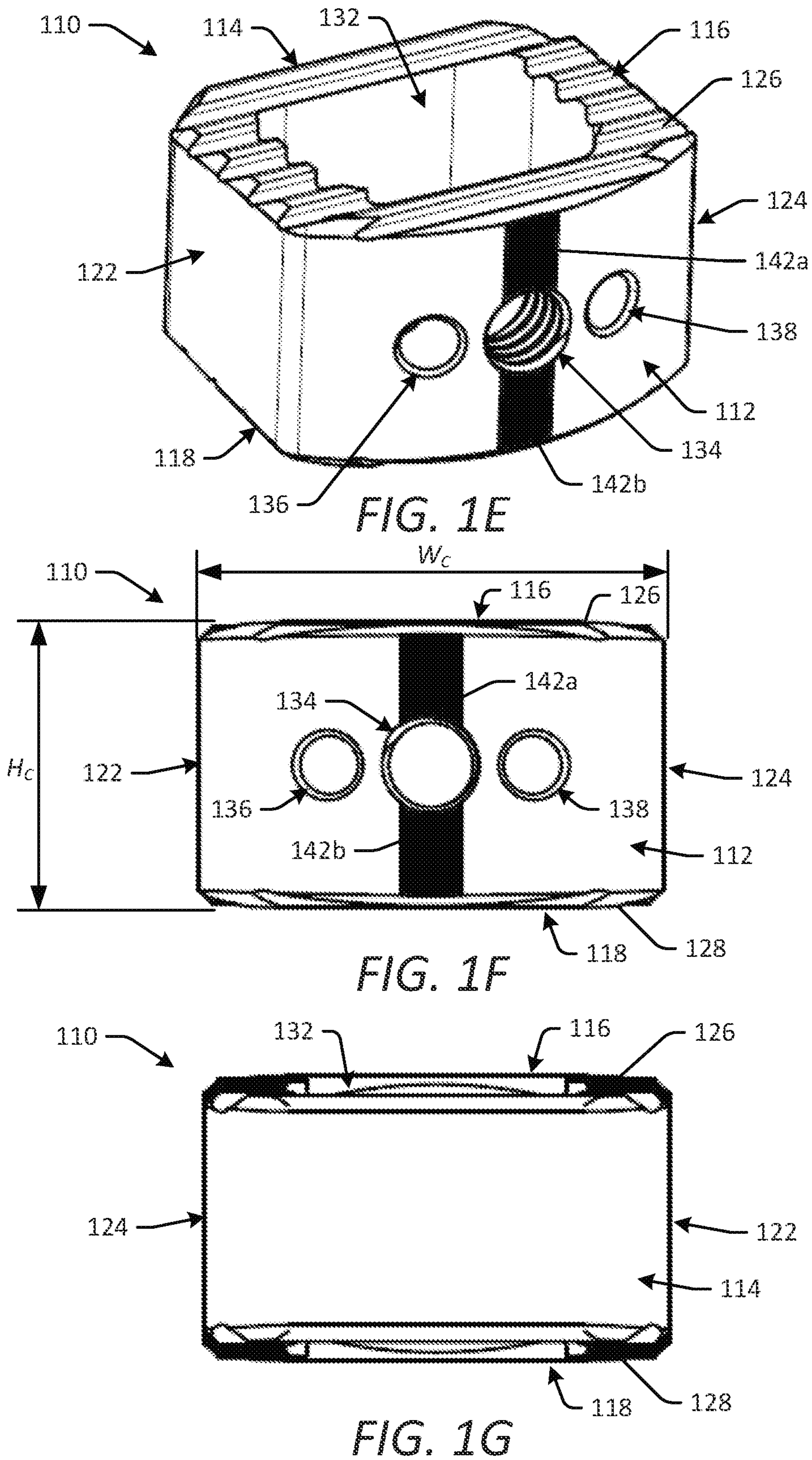
FIG. 1E is a perspective view of the cage of the implantable construct of FIG. 1A.
FIG. 1F is a front view of the cage of the implantable construct of FIG. 1A.
FIG. 1G is a back view of the cage of the implantable construct of FIG. 1A.
Figure 1H:
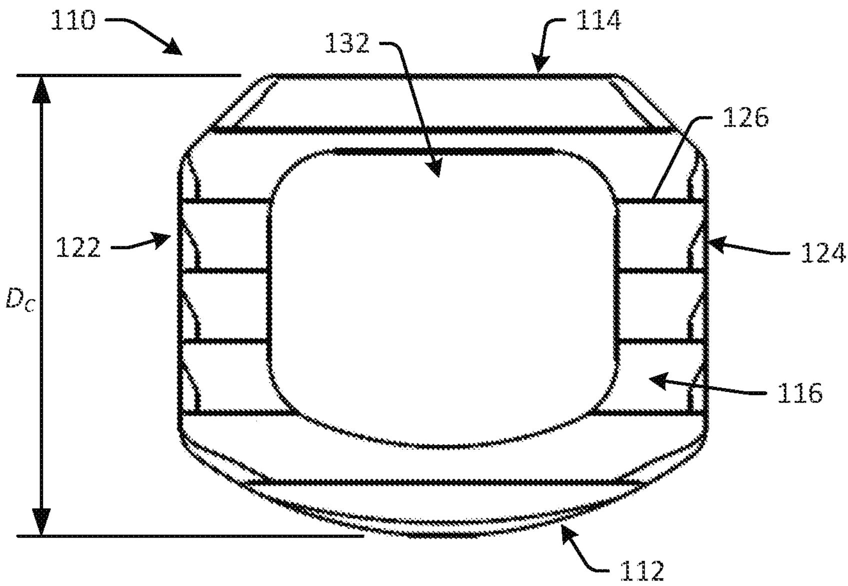
FIG. 1H is a top view of the cage of the implantable construct of FIG. 1A.
Figure 1I:
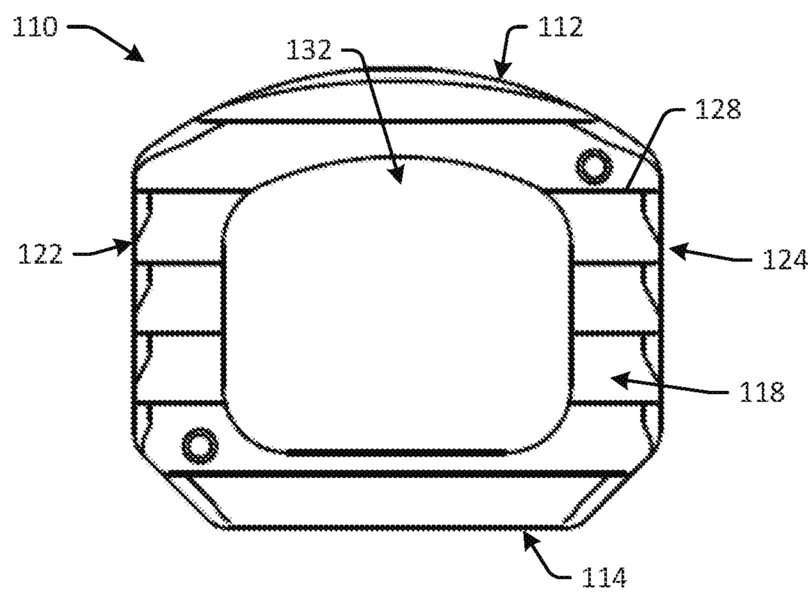
FIG. 1I is a bottom view of the cage of the implantable construct of FIG. 1A.
Figure 1J:
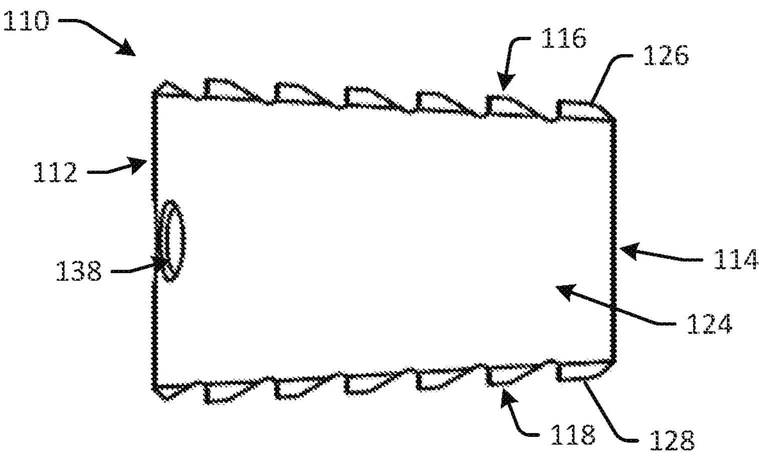
FIG. 1J is a side view of the cage of the implantable construct of FIG. 1A.
Figure 1K:
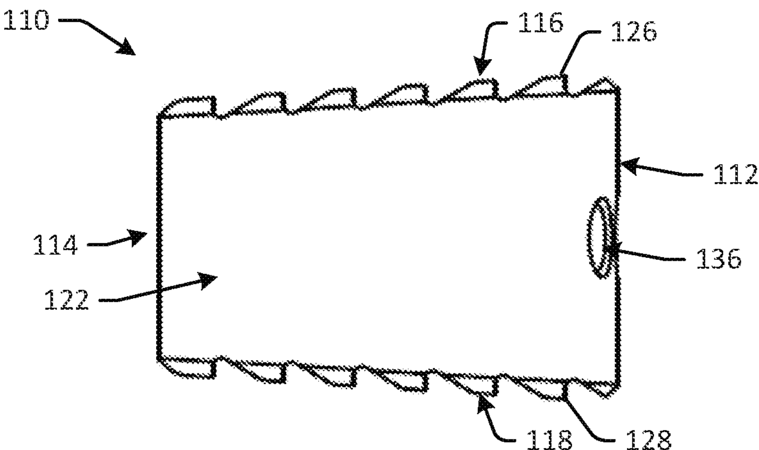
FIG. 1K is a side view of the cage of the implantable construct of FIG. 1A.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

Overview

Embodiments of implantable cages and plates having alignment markings and related methods of using the same are provided. The disclosed cages and plates may be used as part of a construct for stabilizing bone structures of a patient. As described herein, alignment markings of a cage and alignment markings of a plate may be used during a surgical procedure to facilitate alignment of the plate relative to the cage. In carrying out a surgical procedure, the cage may be positioned between a first bone structure and a second bone structure, and the plate may be positioned over the cage, with the alignment markings being used to align the plate with the cage in a desired manner. After aligning the plate with the cage, as desired, the plate may be secured to each of the first bone structure and the second bone structure using implantable screws of other types of mechanical fasteners.

As described herein, an implantable construct for stabilizing a first bone structure and a second bone structure of a patient generally may include a cage configured for positioning between the first bone structure and the second bone structure and a plate configured for positioning over the cage and being secured to each of the first bone structure and the second bone structure. The cage may include one or more cage alignment markings disposed on an exterior surface of the cage, and the plate may include one or more plate alignment markings disposed on an exterior surface of the plate and configured for being aligned with the one or more cage alignment markings such that the plate is aligned with the cage. In some embodiments, the one or more cage alignment markings may include one or more cage alignment lines, and the one or more plate alignment markings may include one or more plate alignment lines, although other types of cage alignment markings and plate alignment markings may be used in other embodiments. In various embodiments, the one or more cage alignment lines may include one or more cage alignment lines extending in a direction of a height of the cage, one or more cage alignment lines extending in a direction of a width of the cage, and/or one or more cage alignment lines extending in a direction transverse to each of the height and the width of the cage. Similarly, in various embodiments, the one or more plate alignment lines may include one or more plate alignment lines extending in a direction of a length of the plate, one or more plate alignment lines extending in a direction of a width of the plate, and/or one or more plate alignment lines extending in a direction transverse to each of the length and the width of the plate.

As discussed above, when using certain existing implantable cages and plates, a surgeon may inadvertently implant a plate at an orientation that is slanted relative to a cage over which the plate is positioned. Although the slanted orientation may be clinically irrelevant, the surgeon may prefer that the plate be aligned with the cage. In some instances, when the surgeon positions the plate over the cage, it may be challenging for the surgeon to visualize how the plate is oriented relative to the cage. For example, blood or tissue at the surgical site may obstruct direct visualization of the cage or the plate and/or the cage or the plate may be formed of materials that are not readily discernable using medical imaging during the procedure. Thus, it may be challenging for the surgeon to align the plate with the cage. As described herein, the alignment markings of the present implantable cages and plates advantageously may be used to facilitate alignment of a plate positioned over a cage, thereby avoiding the plate being implanted in a slanted orientation relative to the cage.

In some embodiments, the cages and plates described herein may be configured for use in a spinal procedure for stabilizing a first vertebra and an adjacent second vertebra. For example, the cages may be spinal cages, such as anterior spinal cages, and the plates may be spinal plates, such as anterior spinal plates. In other embodiments, the cages and plates may be configured for use in other types of surgical procedures for stabilizing bone structures of other portions of a patient's body. Various implementations of the cages and plates may be used.

Still other benefits and advantages of the implantable cages and plates and related methods provided herein over existing cages and plates and methods of their use will be appreciated by those of ordinary skill in the art from the following description and the appended drawings.

Example Implantable Cages and Plates and Related Methods

Referring now to FIGS. 1A-1D, an example implantable construct 100 in accordance with embodiments of the disclosure is depicted. As described below, the construct 100 may be implanted during a surgical procedure for stabilizing bone structures of a patient. In some embodiments, the construct 100 may be implanted during a spinal procedure for stabilizing adjacent vertebrae of a patient, although the construct 100 may be implanted during other types of surgical procedures for stabilizing bone structures of other portions of a patient's body. As shown, the construct 100 may include an implantable cage 110, an implantable plate 150, and a plurality of implantable screws 190. FIGS. 1E-1K show detailed views of the cage 110 in isolation from the other components. It will be appreciated that the illustrated configurations of the cage 110, the plate 150, and the screws 190 are merely examples, and that other configurations of the cage 110, the plate 150, and the screws 190 may be used in various embodiments.

The cage 110 (which also may be referred to as a "spinal cage," an "anterior spinal cage," an "interbody cage," or an "interbody device") may be configured for positioning between a first bone structure and a second bone structure of a patient. In some embodiments in which the construct 100 is used for a spinal procedure, the cage 110 may be configured for positioning between a first vertebra and an adjacent second vertebra (i.e., within the interbody space between the first vertebra and the second vertebra) of the patient. In some such embodiments, the cage 110 may be configured for positioning between the first vertebra and the second vertebra using an anterior approach. The cage 110 may have a front side 112 (which also may be referred to as an "anterior side" or a "first side") and a back side 114 (which also may be referred to as a "posterior side" or a "second side") disposed opposite one another, a top side 116 (which also may be referred to as a "superior side" or a "third side") and a bottom side 118 (which also may be referred to as an "inferior side" or a "fourth side") disposed opposite one another, and a first lateral side 122 (which also may be referred to as a "fifth side") and a second lateral side 124 (which also may be referred to as a "sixth side") disposed opposite one another. As shown, the cage 110 may have a height $H_C$ between the top side 116 and the bottom side 118, a width $W_C$ between the first lateral side 122 and the second lateral side 124, and a depth $D_C$ between the front side 112 and the back side 114.

In some embodiments, as shown, the cage 110 may include one or more features configured for engaging the bone structures between which the cage 110 is positioned during use. According to the illustrated example, the cage 110 may include a plurality of first protrusions 126 disposed along the top side 116 of the cage 110 and configured for engaging the first bone structure and a plurality of second protrusions 128 disposed along the bottom side of the cage and configured for engaging the second bone structure. In some embodiments in which the construct 100 is used for a spinal procedure, the first protrusions 126 may be configured for engaging the superior vertebra, and the second protrusions 128 may be configured for engaging the inferior vertebra. In some embodiments, as shown, the first protrusions 126 and the second protrusions 128 may be formed as ribs extending in the direction of the width $W_C$ of the cage 110. Various other configurations and arrangements of the first protrusions 126 and the second protrusions 128 may be used in other embodiments.

In some embodiments, as shown, the cage 110 may include one or more openings configured for receiving and containing graft material therein and/or for facilitating engagement of the cage 110 with an instrument, such as an insertion instrument used for positioning the cage 110 between bone structures during a surgical procedure. According to the illustrated example, the cage 110 may include an internal opening 132 extending from the top side 116 to the bottom side 118. The internal opening 132 may be configured for receiving and containing graft material therein. In some embodiments, the cage 110 also may include a plurality of openings defined in the front surface of the cage 110 and extending from the front surface to the internal opening 132. As shown, the cage 110 may include a central opening 134 that is centered in the direction of the height $H_C$ of the cage 110 and in the direction of the width $W_C$ of the cage 110, a first lateral opening 136 that is centered in the direction of the height $H_C$ of the cage 110 and spaced apart from the central opening 134 toward the first lateral side 122 in the direction of the width $W_C$ of the cage 110, and a second lateral opening 138 that is that is centered in the direction of the height $H_C$ of the cage 110 and spaced apart from the central opening 134 toward the second lateral side 124 in the direction of the width $W_C$ of the cage 110. The central opening 134, the first lateral opening 136, and the second lateral opening 138 may be configured for receiving mating features of an insertion instrument during implantation of the cage. In some embodiments, the central opening 134 may be threaded, and the lateral openings 136, 138 may have smooth bores without threading, although other configurations of the central opening 134 and the lateral openings 136, 138 may be used in other embodiments.

The cage 110 may include one or more cage alignment markings disposed on an exterior surface of the cage 110 and configured for being aligned with one or more plate alignment markings of the plate 150, as described below. As shown, the cage 110 may include a first cage alignment marking **142*a* (which also may be referred to as a "first cage alignment line") and a second cage alignment marking 142*b* (which also may be referred to as a "second cage alignment line") disposed on the front surface of the cage 110. In some embodiments, as shown, the cage alignment markings 142*a*, 142*b* may be formed as lines or bands each extending in a linear manner. In some embodiments, as shown, the cage alignment markings 142*a*, 142*b* each may extend in the direction of the height $H_C$ of the cage 110. In some embodiments, as shown, the first cage alignment marking 142*a* and the second cage alignment marking 142*b* may be aligned with one another in the direction of the height $H_C$ of the cage 110. In some embodiments, as shown, the first cage alignment marking 142*a* and the second cage alignment marking 142*b* may be centered on the front surface of the cage 110 in the direction of the width $W_C$ of the cage 110. In some embodiments, as shown, the central opening 134 may be disposed between the first cage alignment marking 142*a* and the second cage alignment marking 142*b* in the direction of the height $H_C$ of the cage 110. In some embodiments, the cage alignment markings 142*a*, 142*b* may be laser markings, such as laser etched markings or laser engraved markings, although other suitable forms of the cage alignment markings 142*a*, 142*b* may be used in other embodiments. In some embodiments, the body of the cage 110 may be formed of polyether ether ketone (PEEK), although other suitable materials for the cage 110** may be used in other embodiments.

The plate 150 (which also may be referred to as a "spinal plate" or an "anterior spinal plate") may be configured for positioning over the cage 110 and respective portions of the first bone structure and the second bone structure and being secured to each of the first bone structure and the second bone structure by the screws 190. In some embodiments in which the construct 100 is used for a spinal procedure, the plate 150 may be configured for positioning over respective portions of the first vertebra and the second vertebra and being secured to each of the first vertebra and the second vertebra by the screws 190. In some such embodiments, the plate 150 may be configured for positioning over respective portions of the first vertebra and the second vertebra and being secured to each of the first vertebra and the second vertebra using an anterior approach. The plate 150 may have a front side 152 (which also may be referred to as an "anterior side" or a "first side") and a back side 154 (which also may be referred to as a "posterior side" or a "second side") disposed opposite one another, a top end 156 (which also may be referred to as a "superior end" or a "first end") and a bottom end 158 (which also may be referred to as an "inferior end" or a "second end") disposed opposite one another, and a first lateral side 162 (which also may be referred to as a "third side") and a second lateral side 164 (which also may be referred to as a "fourth side") disposed opposite one another. As shown, the plate 150 may have a length $L_P$ between the top end 156 and the bottom end 158, a width $W_P$ between the first lateral side 162 and the second lateral side 164, and a thickness $T_P$ between the front side 152 and the back side 154.

In some embodiments, as shown, the plate 150 may include one or more openings configured for receiving the screws 190 therethrough and/or for allowing visualization of the cage 110 therethrough when the plate 150 is positioned over the cage 110 during a surgical procedure. According to the illustrated example, the plate 150 may include a plurality of screw openings 172 each extending from the front surface to the back surface of the plate 150 and configured for receiving one of the screws 190 therethrough for securing the plate 150 to the bone structures of the patient. As shown, the plate 150 may include a first pair of the screw openings 172 disposed near the top end 156 and a second pair of the screw openings 172 disposed near the bottom end 158. In some embodiments, the plate 150 also may include a central opening 174 extending from the front surface to the back surface of the plate 150 and configured for allowing visualization of the cage 110 therethrough when the plate 150 is positioned over the cage 110. As shown, the central opening 174 may be centered in the direction of the length $L_P$ of the plate 150 and in the direction of the width $W_P$ of the plate 150. In some embodiments, as shown, the plate 150 may include a pair of blocking members 176 that are rotatably coupled to the body of the plate 150 and configured for inhibiting the screws 190 from backing out of the bone structures after implantation. In particular, each of the blocking members 176 may be configured for rotating between an unblocked position, in which the blocking member 176 allows the screws 190 to be advanced through the adjacent screw openings 172 into the bone structures, and a blocked position, in which tabs of the blocking member 176 inhibit the screws 190 from backing out of the bone structures.

The plate 150 may include one or more plate alignment markings disposed on an exterior surface of the plate 150 and configured for being aligned with the one or more cage alignment markings of the cage 110. As shown, the plate 150 may include a first plate alignment marking 182*a* (which also may be referred to as a "first plate alignment line"), a second plate alignment marking 182*b* (which also may be referred to as a "second plate alignment line"), a third plate alignment marking 182*c* (which also may be referred to as a "third plate alignment line"), and a fourth plate alignment marking 182*d* (which also may be referred to as a "fourth plate alignment line") disposed on the front surface of the plate 150. In some embodiments, as shown, the plate alignment markings 182*a*, 182*b*, 182*c*, 182*d* may be formed as lines or bands each extending in a linear manner. In some embodiments, as shown, the plate alignment markings 182*a*, 182*b*, 182*c*, 182*d* each may extend in the direction of the length $L_P$ of the plate 150. In some embodiments, as shown, the plate alignment markings 182*a*, 182*b*, 182*c*, 182*d* may be aligned with one another in the direction of the length $L_P$ of the plate 150. In some embodiments, as shown, the plate alignment markings 182*a*, 182*b*, 182*c*, 182*d* may be centered on the front surface of the plate 150 in the direction of the width $W_P$ of the plate 150. In some embodiments, as shown, the central opening 174 may be disposed between the first plate alignment marking 182*a* and the second plate alignment marking 182*b* in the direction of the length $L_P$ of the plate 150. In some embodiments, as shown, one of the blocking members 176 may be disposed between the first plate alignment marking 182*a* and the third plate alignment marking 182*c* in the direction of the length $L_P$ of the plate 150, and the other blocking member 176 may be disposed between the second plate alignment marking 182*b* and the fourth plate alignment marking 182*d* in the direction of the length $L_P$ of the plate 150. In some embodiments, the plate alignment markings 182*a*, 182*b*, 182*c*, 182*d* may be laser markings, such as laser etched markings or laser engraved markings, although other suitable forms of the plate alignment markings 182*a*, 182*b*, 182*c*, 182*d* may be used in other embodiments. In some embodiments, the body of the plate 150 may be formed of titanium, although other suitable materials for the plate 150 may be used in other embodiments.

As mentioned above, the implantable construct 100 may be used for stabilizing a first bone structure and a second bone structure of a patient. In some embodiments, the first bone structure may be a first vertebra, and the second bone structure may be an adjacent second vertebra. During implantation of the construct 100, the cage 110 may be positioned between the first bone structure and the second bone structure. Then, the plate 150 may be positioned over the cage 110 and over respective portions of the first bone structure and the second bone structure. While positioning the plate 150, the cage alignment markings 142*a*, 142*b* and the plate alignment markings 182*a*, 182*b*, 182*c*, 182*d* may be used to align the plate 150 with the cage 110. In particular, the plate alignment markings 182*a*, 182*b*, 182*c*, 182*d* may be aligned with the cage alignment markings 142*a*, 142*b* in the direction of the height $H_C$ of the cage 110, as shown in FIG. 1B, such that the plate 150 is aligned with the cage 110. While maintaining such alignment of the plate 150 with the cage 110, the screws 190 may be advanced through the respective screw openings 172 and into the bone structures, thereby securing the plate 150 to each of the first bone structure and the second bone structure.

Figures 2A, 2B:
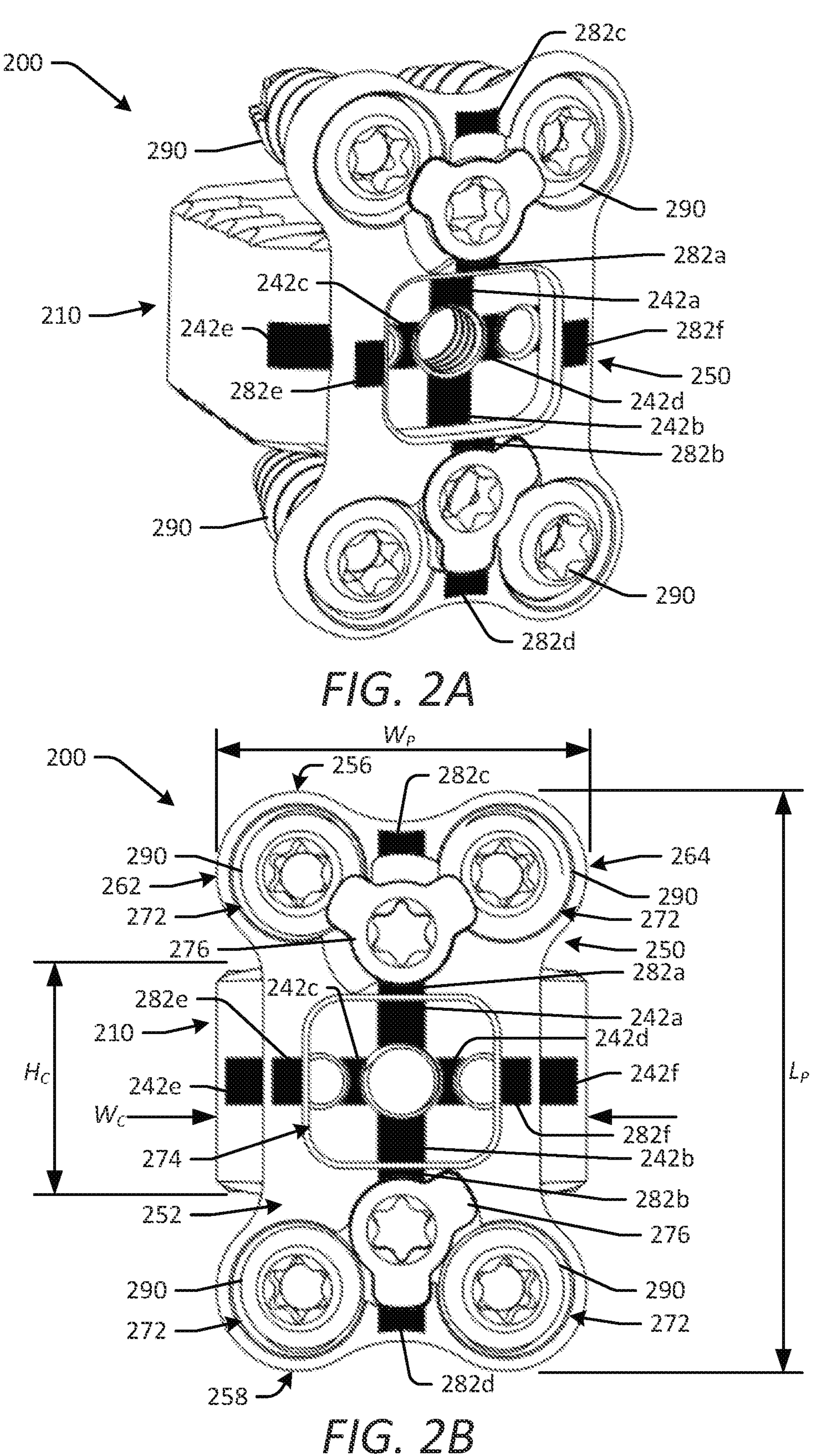
FIG. 2A is a perspective view of an example implantable construct in accordance with embodiments of the disclosure, showing a cage, a plate, and screws of the implantable construct.
FIG. 2B is a front view of the implantable construct of FIG. 2A.
Figure 2C:
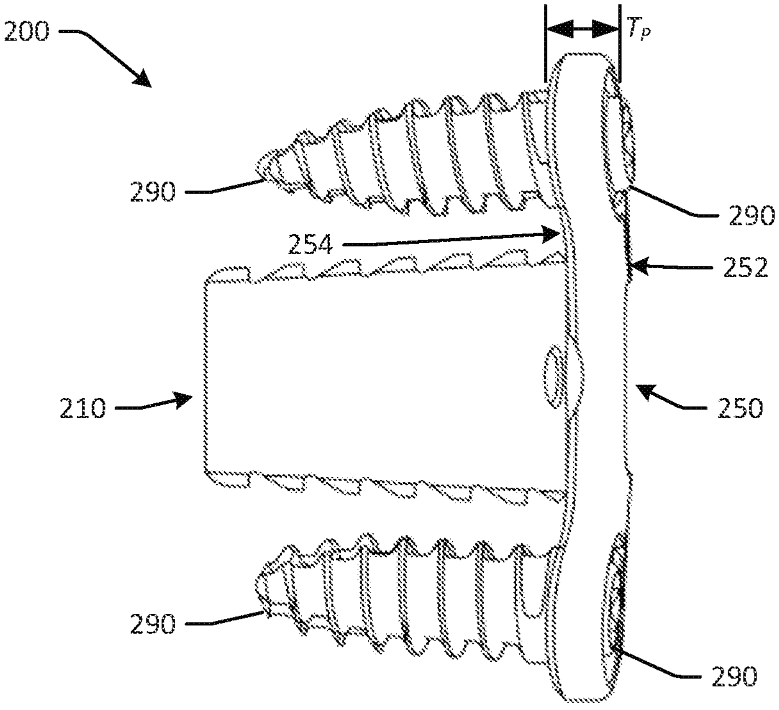
FIG. 2C is a side view of the implantable construct of FIG. 2A.
Figures 2D, 2E, 2F:
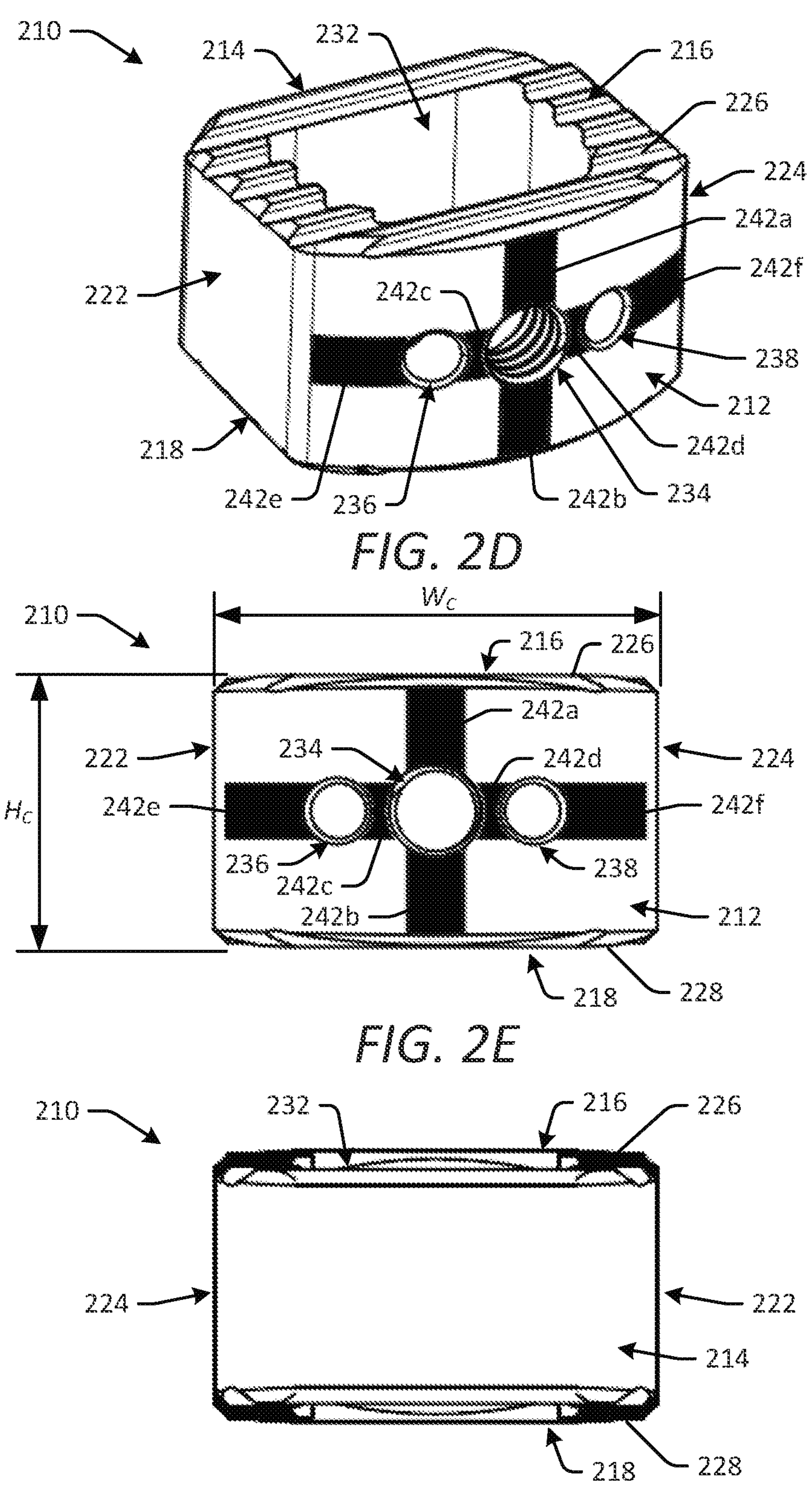
FIG. 2D is a perspective view of the cage of the implantable construct of FIG. 2A.
FIG. 2E is a front view of the cage of the implantable construct of FIG. 2A.
FIG. 2F is a back view of the cage of the implantable construct of FIG. 2A.
Figure 2G:
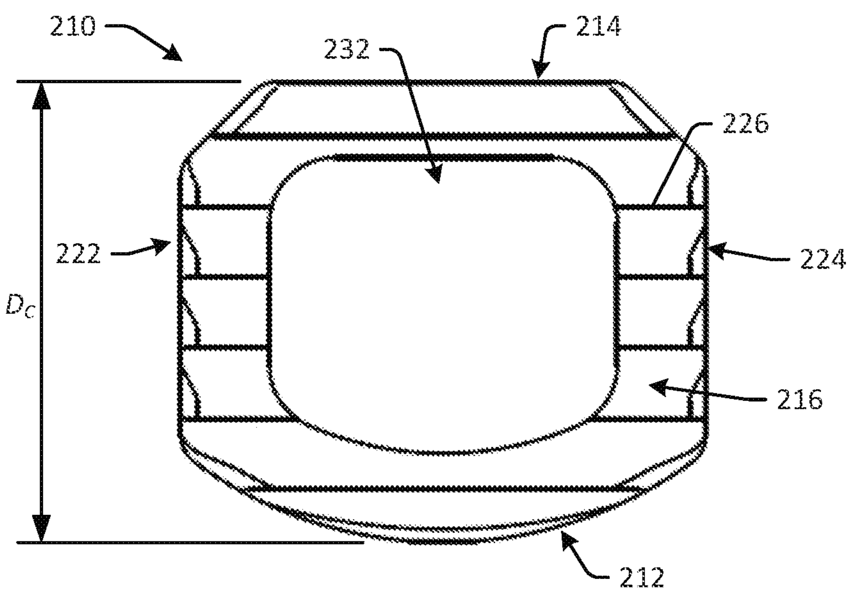
FIG. 2G is a top view of the cage of the implantable construct of FIG. 2A.
Figure 2H:
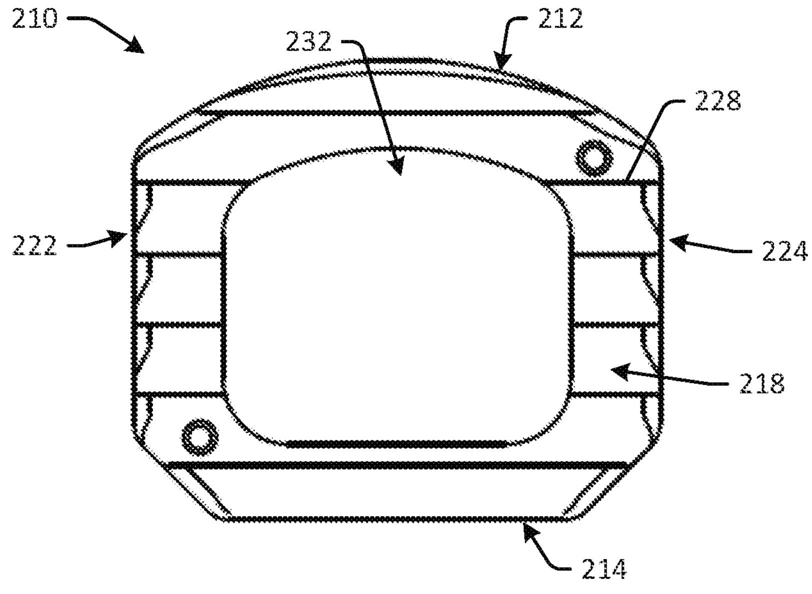
FIG. 2H is a bottom view of the cage of the implantable construct of FIG. 2A.
Figure 2I:
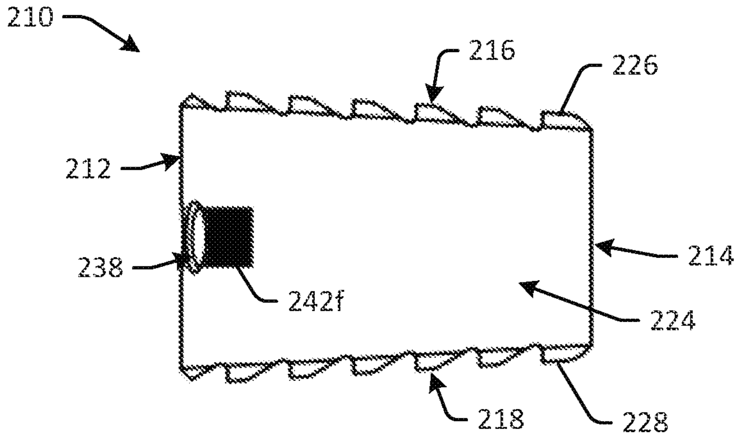
FIG. 2I is a side view of the cage of the implantable construct of FIG. 2A.
Figure 2J:
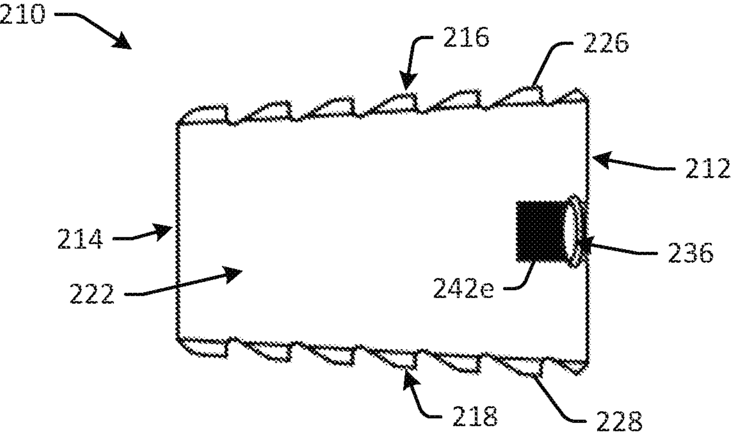
FIG. 2J is a side view of the cage of the implantable construct of FIG. 2A.

FIGS. 2A-2C depict another example implantable construct 200 in accordance with embodiments of the disclosure. As described below, the construct 200 may be implanted during a surgical procedure for stabilizing bone structures of a patient. In some embodiments, the construct 200 may be implanted during a spinal procedure for stabilizing adjacent vertebrae of a patient, although the construct 200 may be implanted during other types of surgical procedures for stabilizing bone structures of other portions of a patient's body. As shown, the construct 200 may include an implantable cage 210, an implantable plate 250, and a plurality of implantable screws 290. FIGS. 2D-2J show detailed views of the cage 210 in isolation from the other components. It will be appreciated that the illustrated configurations of the cage 210, the plate 250, and the screws 290 are merely examples, and that other configurations of the cage 210, the plate 250, and the screws 290 may be used in various embodiments. Certain similarities and differences between the construct 200 and the construct 100 will be appreciated from the drawings and the following description. Particular differences relate to configurations of cage alignment markings of the cage 210 and plate alignment markings of the plate 250.

The cage 210 (which also may be referred to as a "spinal cage," an "anterior spinal cage," an "interbody cage," or an "interbody device") may be configured for positioning between a first bone structure and a second bone structure of a patient. In some embodiments in which the construct 200 is used for a spinal procedure, the cage 210 may be configured for positioning between a first vertebra and an adjacent second vertebra (i.e., within the interbody space between the first vertebra and the second vertebra) of the patient. In some such embodiments, the cage 210 may be configured for positioning between the first vertebra and the second vertebra using an anterior approach. The cage 210 may have a front side 212 (which also may be referred to as an "anterior side" or a "first side") and a back side 214 (which also may be referred to as a "posterior side" or a "second side") disposed opposite one another, a top side 216 (which also may be referred to as a "superior side" or a "third side") and a bottom side 218 (which also may be referred to as an "inferior side" or a "fourth side") disposed opposite one another, and a first lateral side 222 (which also may be referred to as a "fifth side") and a second lateral side 224 (which also may be referred to as a "sixth side") disposed opposite one another. As shown, the cage 210 may have a height $H_C$ between the top side 216 and the bottom side 218, a width $W_C$ between the first lateral side 222 and the second lateral side 224, and a depth $D_C$ between the front side 212 and the back side 214.

In some embodiments, as shown, the cage 210 may include one or more features configured for engaging the bone structures between which the cage 210 is positioned during use. According to the illustrated example, the cage 210 may include a plurality of first protrusions 226 disposed along the top side 216 of the cage 210 and configured for engaging the first bone structure and a plurality of second protrusions 228 disposed along the bottom side of the cage and configured for engaging the second bone structure. In some embodiments in which the construct 200 is used for a spinal procedure, the first protrusions 226 may be configured for engaging the superior vertebra, and the second protrusions 228 may be configured for engaging the inferior vertebra. In some embodiments, as shown, the first protrusions 226 and the second protrusions 228 may be formed as ribs extending in the direction of the width $W_C$ of the cage 210. Various other configurations and arrangements of the first protrusions 226 and the second protrusions 228 may be used in other embodiments.

In some embodiments, as shown, the cage 210 may include one or more openings configured for receiving and containing graft material therein and/or for facilitating engagement of the cage 210 with an instrument, such as an insertion instrument used for positioning the cage 210 between bone structures during a surgical procedure. According to the illustrated example, the cage 210 may include an internal opening 232 extending from the top side 216 to the bottom side 218. The internal opening 232 may be configured for receiving and containing graft material therein. In some embodiments, the cage 210 also may include a plurality of openings defined in the front surface of the cage 210 and extending from the front surface to the internal opening 232. As shown, the cage 210 may include a central opening 234 that is centered in the direction of the height $H_C$ of the cage 210 and in the direction of the width $W_C$ of the cage 210, a first lateral opening 236 that is centered in the direction of the height $H_C$ of the cage 210 and spaced apart from the central opening 234 toward the first lateral side 222 in the direction of the width $W_C$ of the cage 210, and a second lateral opening 238 that is that is centered in the direction of the height $H_C$ of the cage 210 and spaced apart from the central opening 234 toward the second lateral side 224 in the direction of the width $W_C$ of the cage 210. The central opening 234, the first lateral opening 236, and the second lateral opening 238 may be configured for receiving mating features of an insertion instrument during implantation of the cage. In some embodiments, the central opening 234 may be threaded, and the lateral openings 236, 238 may have smooth bores without threading, although other configurations of the central opening 234 and the lateral openings 236, 238 may be used in other embodiments.

The cage 210 may include one or more cage alignment markings disposed on an exterior surface of the cage 210 and configured for being aligned with one or more plate alignment markings of the plate 250, as described below. As shown, the cage 210 may include a first cage alignment marking **242*a* (which also may be referred to as a "first cage alignment line"), a second cage alignment marking 242*b* (which also may be referred to as a "second cage alignment line"), a third cage alignment marking 242*c* (which also may be referred to as a "third cage alignment line"), a fourth cage alignment marking 242*d* (which also may be referred to as a "fourth cage alignment line"), a fifth cage alignment marking 242*e* (which also may be referred to as a "fifth cage alignment line"), and a sixth cage alignment marking 242*f* (which also may be referred to as a "sixth cage alignment line") disposed on the front surface of the cage 210. In some embodiments, as shown, the cage alignment markings 242*a*, 242*b*, 242*c*, 242*d*, 242*e*, 242*f* may be formed as lines or bands each extending in a linear manner. In some embodiments, as shown, the first cage alignment marking 242*a* and the second cage alignment marking 242*b* each may extend in the direction of the height $H_C$ of the cage 210. In some embodiments, as shown, the first cage alignment marking 242*a* and the second cage alignment marking 242*b* may be aligned with one another in the direction of the height $H_C$ of the cage 210. In some embodiments, as shown, the first cage alignment marking 242*a* and the second cage alignment marking 242*b* may be centered on the front surface of the cage 210 in the direction of the width $W_C$ of the cage 210. In some embodiments, as shown, the central opening 234 may be disposed between the first cage alignment marking 242*a* and the second cage alignment marking 242*b* in the direction of the height $H_C$ of the cage 210. In some embodiments, as shown, the third cage alignment marking 242*c*, the fourth cage alignment marking 242*d*, the fifth cage alignment marking 242*e*, and the sixth cage alignment marking 242*f* each may extend in the direction of the width $W_C$ of the cage 210. In some embodiments, as shown, the third cage alignment marking 242*c*, the fourth cage alignment marking 242*d*, the fifth cage alignment marking 242*e*, and the sixth cage alignment marking 242*f* may be aligned with one another in the direction of the width $W_C$ of the cage 210. In some embodiments, as shown, the third cage alignment marking 242*c*, the fourth cage alignment marking 242*d*, the fifth cage alignment marking 242*e*, and the sixth cage alignment marking 242*f* may be centered on the front surface of the cage 210 in the direction of the height $H_C$ of the cage 210. In some embodiments, as shown, the central opening 234 may be disposed between the third cage alignment marking 242*c* and the fourth cage alignment marking 242*d* in the direction of the width $W_C$ of the cage 210, the first lateral opening 236 may be disposed between the third cage alignment marking 242*c* and the fifth cage alignment marking 242*e* in the direction of the width $W_C$ of the cage 210, and the second lateral opening 238 may be disposed between the fourth cage alignment marking 242*d* and the sixth cage alignment marking 242*f* in the direction of the width $W_C$ of the cage 210. In some embodiments, the cage alignment markings 242*a*, 242*b*, 242*c*, 242*d*, 242*e*, 242*f* may be laser markings, such as laser etched markings or laser engraved markings, although other suitable forms of the cage alignment markings 242*a*, 242*b*, 242*c*, 242*d*, 242*e*, 242*f* may be used in other embodiments. In some embodiments, the body of the cage 210 may be formed of polyether ether ketone (PEEK), although other suitable materials for the cage 210** may be used in other embodiments.

The plate 250 (which also may be referred to as a "spinal plate" or an "anterior spinal plate") may be configured for positioning over the cage 210 and respective portions of the first bone structure and the second bone structure and being secured to each of the first bone structure and the second bone structure by the screws 290. In some embodiments in which the construct 200 is used for a spinal procedure, the plate 250 may be configured for positioning over respective portions of the first vertebra and the second vertebra and being secured to each of the first vertebra and the second vertebra by the screws 290. In some such embodiments, the plate 250 may be configured for positioning over respective portions of the first vertebra and the second vertebra and being secured to each of the first vertebra and the second vertebra using an anterior approach. The plate 250 may have a front side 252 (which also may be referred to as an "anterior side" or a "first side") and a back side 254 (which also may be referred to as a "posterior side" or a "second side") disposed opposite one another, a top end 256 (which also may be referred to as a "superior end" or a "first end") and a bottom end 258 (which also may be referred to as an "inferior end" or a "second end") disposed opposite one another, and a first lateral side 262 (which also may be referred to as a "third side") and a second lateral side 264 (which also may be referred to as a "fourth side") disposed opposite one another. As shown, the plate 250 may have a length $L_P$ between the top end 256 and the bottom end 258, a width $W_P$ between the first lateral side 262 and the second lateral side 264, and a thickness $T_P$ between the front side 252 and the back side 254.

In some embodiments, as shown, the plate 250 may include one or more openings configured for receiving the screws 290 therethrough and/or for allowing visualization of the cage 210 therethrough when the plate 250 is positioned over the cage 210 during a surgical procedure. According to the illustrated example, the plate 250 may include a plurality of screw openings 272 each extending from the front surface to the back surface of the plate 250 and configured for receiving one of the screws 290 therethrough for securing the plate 250 to the bone structures of the patient. As shown, the plate 250 may include a first pair of the screw openings 272 disposed near the top end 256 and a second pair of the screw openings 272 disposed near the bottom end 258. In some embodiments, the plate 250 also may include a central opening 274 extending from the front surface to the back surface of the plate 250 and configured for allowing visualization of the cage 210 therethrough when the plate 250 is positioned over the cage 210. As shown, the central opening 274 may be centered in the direction of the length $L_P$ of the plate 250 and in the direction of the width $W_P$ of the plate 150. In some embodiments, as shown, the plate 250 may include a pair of blocking members 276 that are rotatably coupled to the body of the plate 250 and configured for inhibiting the screws 290 from backing out of the bone structures after implantation. In particular, each of the blocking members 276 may be configured for rotating between an unblocked position, in which the blocking member 276 allows the screws 290 to be advanced through the adjacent screw openings 272 into the bone structures, and a blocked position, in which tabs of the blocking member 276 inhibit the screws 290 from backing out of the bone structures.

The plate 250 may include one or more plate alignment markings disposed on an exterior surface of the plate 250 and configured for being aligned with the one or more cage alignment markings of the cage 210. As shown, the plate 250 may include a first plate alignment marking **282*a* (which also may be referred to as a "first plate alignment line"), a second plate alignment marking 282*b* (which also may be referred to as a "second plate alignment line"), a third plate alignment marking 282*c* (which also may be referred to as a "third plate alignment line"), a fourth plate alignment marking 282*d* (which also may be referred to as a "fourth plate alignment line"), a fifth plate alignment marking 282*e* (which also may be referred to as a "fifth plate alignment line"), and a sixth plate alignment marking 282*f* (which also may be referred to as a "sixth plate alignment line") disposed on the front surface of the plate 250. In some embodiments, as shown, the plate alignment markings 282*a*, 282*b*, 282*c*, 282*d*, 282*e*, 282*f* may be formed as lines or bands each extending in a linear manner. In some embodiments, as shown, the first plate alignment marking 282*a*, the second plate alignment marking 282*b*, the third plate alignment marking 282*c*, and the fourth plate alignment marking 282*d* each may extend in the direction of the length $L_P$ of the plate 250. In some embodiments, as shown, the first plate alignment marking 282*a*, the second plate alignment marking 282*b*, the third plate alignment marking 282*c*, and the fourth plate alignment marking 282*d* may be aligned with one another in the direction of the length $L_P$ of the plate 250. In some embodiments, as shown, the first plate alignment marking 282*a*, the second plate alignment marking 282*b*, the third plate alignment marking 282*c*, and the fourth plate alignment marking 282*d* may be centered on the front surface of the plate 250 in the direction of the width $W_P$ of the plate 250. In some embodiments, as shown, the central opening 274 may be disposed between the first plate alignment marking 282*a* and the second plate alignment marking 282*b* in the direction of the length $L_P$ of the plate 250. In some embodiments, as shown, one of the blocking members 276 may be disposed between the first plate alignment marking 282*a* and the third plate alignment marking 282*c* in the direction of the length $L_P$ of the plate 250, and the other blocking member 276 may be disposed between the second plate alignment marking 282*b* and the fourth plate alignment marking 282*d* in the direction of the length $L_P$ of the plate 250. In some embodiments, as shown, the fifth plate alignment marking 282*e* and the sixth plate alignment marking 282*f* each may extend in the direction of the width $W_P$ of the plate 250. In some embodiments, as shown, the fifth plate alignment marking 282*e* and the sixth plate alignment marking 282*f* may be aligned with one another in the direction of the width $W_P$ of the plate 250. In some embodiments, as shown, the fifth plate alignment marking 282*e* and the sixth plate alignment marking 282*f* may be centered on the front surface of the plate 250 in the direction of the length $L_P$ of the plate 250. In some embodiments, as shown, the central opening 274 may be disposed between the fifth plate alignment marking 282*e* and the sixth plate alignment marking 282*f* in the direction of the width $W_P$ of the plate 250. In some embodiments, the plate alignment markings 282*a*, 282*b*, 282*c*, 282*d*, 282*e*, 282*f* may be laser markings, such as laser etched markings or laser engraved markings, although other suitable forms of the plate alignment markings 282*a*, 282*b*, 282*c*, 282*d*, 282*e*, 282*f* may be used in other embodiments. In some embodiments, the body of the plate 250 may be formed of titanium, although other suitable materials for the plate 250** may be used in other embodiments.

As mentioned above, the implantable construct 200 may be used for stabilizing a first bone structure and a second bone structure of a patient. In some embodiments, the first bone structure may be a first vertebra, and the second bone structure may be an adjacent second vertebra. During implantation of the construct 200, the cage 210 may be positioned between the first bone structure and the second bone structure. Then, the plate 250 may be positioned over the cage 210 and over respective portions of the first bone structure and the second bone structure. While positioning the plate 250, the cage alignment markings 242*a*, 242*b*, 242*c*, 242*d*, 242*e*, 242*f* and the plate alignment markings 282*a*, 282*b*, 282*c*, 282*d*, 282*e*, 282*f* may be used to align the plate 250 with the cage 210. In particular, the first plate alignment marking 282*a*, the second plate alignment marking 282*b*, the third plate alignment marking 282*c*, and the fourth plate alignment marking 282*d* may be aligned with the first cage alignment marking 242*a* and the second cage alignment marking 242*b* in the direction of the height $H_C$ of the cage 210, while the fifth plate alignment marking 282*e* and the sixth plate alignment marking 282*f* may be aligned with the third cage alignment marking 242*c*, the fourth cage alignment marking 242*d*, the fifth cage alignment marking 242*e*, and the sixth cage alignment marking 242*f* in the direction of the width $W_C$ of the cage 210, as shown in FIG. 2B, such that the plate 250 is aligned with the cage 210. While maintaining such alignment of the plate 250 with the cage 210, the screws 290 may be advanced through the respective screw openings 272 and into the bone structures, thereby securing the plate 250 to each of the first bone structure and the second bone structure.

Figure 3:
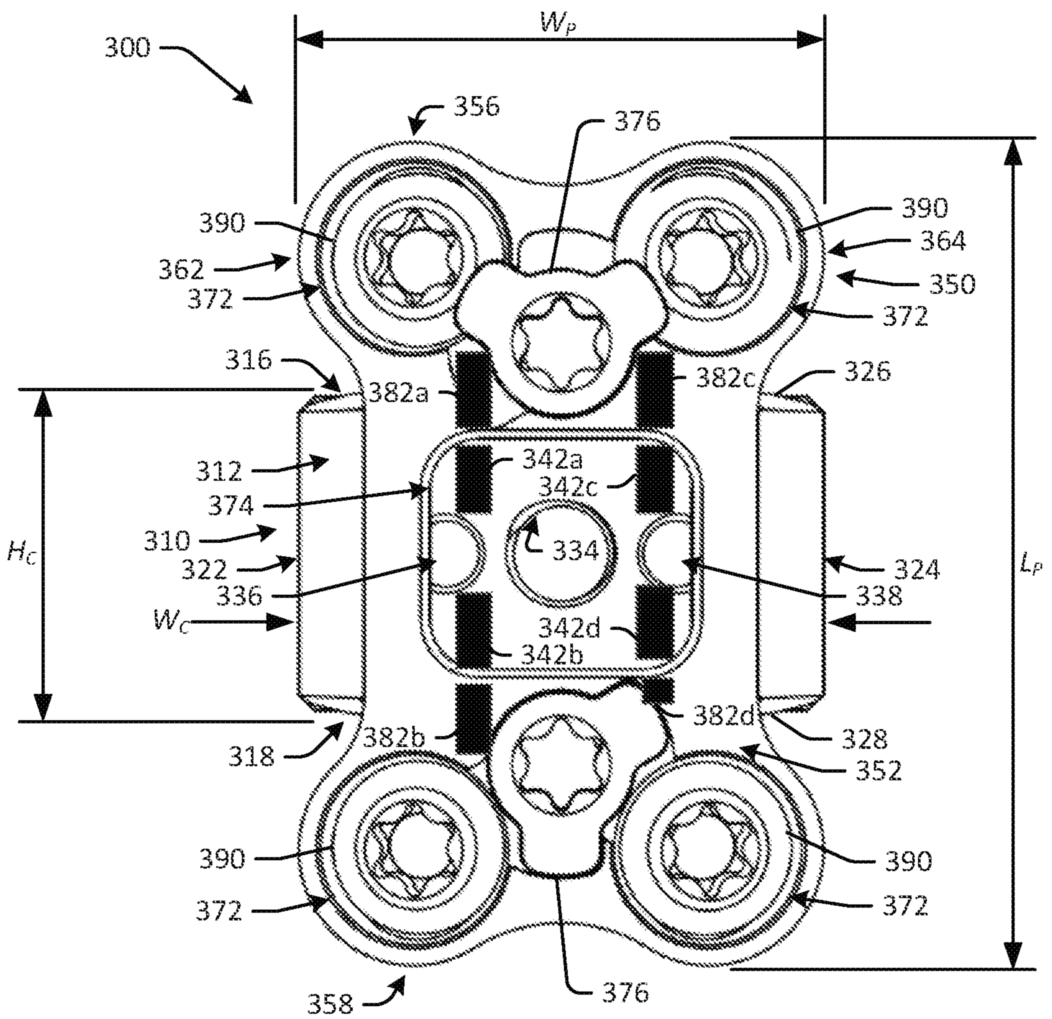
FIG. 3 is a perspective view of an example implantable construct in accordance with embodiments of the disclosure, showing a cage, a plate, and screws of the implantable construct.

FIG. 3 depicts another example implantable construct 300 in accordance with embodiments of the disclosure. As described below, the construct 300 may be implanted during a surgical procedure for stabilizing bone structures of a patient. In some embodiments, the construct 300 may be implanted during a spinal procedure for stabilizing adjacent vertebrae of a patient, although the construct 300 may be implanted during other types of surgical procedures for stabilizing bone structures of other portions of a patient's body. As shown, the construct 300 may include an implantable cage 310, an implantable plate 350, and a plurality of implantable screws 390. It will be appreciated that the illustrated configurations of the cage 310, the plate 350, and the screws 390 are merely examples, and that other configurations of the cage 310, the plate 350, and the screws 390 may be used in various embodiments. Certain similarities and differences between the construct 300 and the construct 100 will be appreciated from the drawings and the following description. Particular differences relate to configurations of cage alignment markings of the cage 310 and plate alignment markings of the plate 350.

The cage 310 (which also may be referred to as a "spinal cage," an "anterior spinal cage," an "interbody cage," or an "interbody device") may be configured for positioning between a first bone structure and a second bone structure of a patient. In some embodiments in which the construct 300 is used for a spinal procedure, the cage 310 may be configured for positioning between a first vertebra and an adjacent second vertebra (i.e., within the interbody space between the first vertebra and the second vertebra) of the patient. In some such embodiments, the cage 310 may be configured for positioning between the first vertebra and the second vertebra using an anterior approach. The cage 310 may have a front side 312 (which also may be referred to as an "anterior side" or a "first side") and a back side (which also may be referred to as a "posterior side" or a "second side") disposed opposite one another, a top side 316 (which also may be referred to as a "superior side" or a "third side") and a bottom side 318 (which also may be referred to as an "inferior side" or a "fourth side") disposed opposite one another, and a first lateral side 322 (which also may be referred to as a "fifth side") and a second lateral side 324 (which also may be referred to as a "sixth side") disposed opposite one another. As shown, the cage 310 may have a height $H_C$ between the top side 316 and the bottom side 318, a width $W_C$ between the first lateral side 322 and the second lateral side 324, and a depth between the front side 312 and the back side.

In some embodiments, as shown, the cage 310 may include one or more features configured for engaging the bone structures between which the cage 310 is positioned during use. According to the illustrated example, the cage 310 may include a plurality of first protrusions 326 disposed along the top side 316 of the cage 310 and configured for engaging the first bone structure and a plurality of second protrusions 328 disposed along the bottom side of the cage and configured for engaging the second bone structure. In some embodiments in which the construct 300 is used for a spinal procedure, the first protrusions 326 may be configured for engaging the superior vertebra, and the second protrusions 328 may be configured for engaging the inferior vertebra. In some embodiments, as shown, the first protrusions 326 and the second protrusions 328 may be formed as ribs extending in the direction of the width $W_C$ of the cage 310. Various other configurations and arrangements of the first protrusions 326 and the second protrusions 328 may be used in other embodiments.

In some embodiments, as shown, the cage 310 may include one or more openings configured for receiving and containing graft material therein and/or for facilitating engagement of the cage 310 with an instrument, such as an insertion instrument used for positioning the cage 310 between bone structures during a surgical procedure. According to the illustrated example, the cage 310 may include an internal opening extending from the top side 316 to the bottom side 318. The internal opening may be configured for receiving and containing graft material therein. In some embodiments, the cage 310 also may include a plurality of openings defined in the front surface of the cage 310 and extending from the front surface to the internal opening. As shown, the cage 310 may include a central opening 334 that is centered in the direction of the height $H_C$ of the cage 310 and in the direction of the width $W_C$ of the cage 310, a first lateral opening 336 that is centered in the direction of the height $H_C$ of the cage 310 and spaced apart from the central opening 334 toward the first lateral side 322 in the direction of the width $W_C$ of the cage 310, and a second lateral opening 338 that is that is centered in the direction of the height $H_C$ of the cage 310 and spaced apart from the central opening 334 toward the second lateral side 324 in the direction of the width $W_C$ of the cage 310. The central opening 334, the first lateral opening 336, and the second lateral opening 338 may be configured for receiving mating features of an insertion instrument during implantation of the cage. In some embodiments, the central opening 334 may be threaded, and the lateral openings 336, 338 may have smooth bores without threading, although other configurations of the central opening 334 and the lateral openings 336, 338 may be used in other embodiments.

The cage 310 may include one or more cage alignment markings disposed on an exterior surface of the cage 310 and configured for being aligned with one or more plate alignment markings of the plate 350, as described below. As shown, the cage 310 may include a first cage alignment marking 342*a* (which also may be referred to as a "first cage alignment line"), a second cage alignment marking 342*b*

(which also may be referred to as a “second cage alignment line”), a third cage alignment marking 342*c* (which also may be referred to as a “third cage alignment line”), and a fourth cage alignment marking 342*d* (which also may be referred to as a “fourth cage alignment line”) disposed on the front surface of the cage 310. In some embodiments, as shown, the cage alignment markings 342*a*, 342*b*, 342*c*, 342*d* may be formed as lines or bands each extending in a linear manner. In some embodiments, as shown, the cage alignment markings 342*a*, 342*b*, 342*c*, 342*d* each may extend in the direction of the height $H_C$ of the cage 310. In some embodiments, as shown, the first cage alignment marking 342*a* and the second cage alignment marking 342*b* may be aligned with one another in the direction of the height $H_C$ of the cage 310, and the third cage alignment marking 342*c* and the fourth cage alignment marking 342*d* may be aligned with one another in the direction of the height $H_C$ of the cage 310. In some embodiments, as shown, the first cage alignment marking 342*a* and the second cage alignment marking 342*b* may be spaced apart from the third cage alignment marking 342*c* and the fourth cage alignment marking 342*d* on the front surface of the cage 310 in the direction of the width $W_C$ of the cage 310. In some embodiments, as shown, the first lateral opening 336 may be disposed between the first cage alignment marking 342*a* and the second cage alignment marking 342*b* in the direction of the height $H_C$ of the cage 310, and the second lateral opening 338 may be disposed between the third cage alignment marking 342*c* and the fourth cage alignment marking 342*d* in the direction of the height $H_C$ of the cage 310. In some embodiments, the cage alignment markings 342*a*, 342*b*, 342*c*, 342*d* may be laser markings, such as laser etched markings or laser engraved markings, although other suitable forms of the cage alignment markings 342*a*, 342*b*, 342*c*, 342*d* may be used in other embodiments. In some embodiments, the body of the cage 310 may be formed of polyether ether ketone (PEEK), although other suitable materials for the cage 310 may be used in other embodiments.

The plate 350 (which also may be referred to as a “spinal plate” or an “anterior spinal plate”) may be configured for positioning over the cage 310 and respective portions of the first bone structure and the second bone structure and being secured to each of the first bone structure and the second bone structure by the screws 390. In some embodiments in which the construct 300 is used for a spinal procedure, the plate 350 may be configured for positioning over respective portions of the first vertebra and the second vertebra and being secured to each of the first vertebra and the second vertebra by the screws 390. In some such embodiments, the plate 350 may be configured for positioning over respective portions of the first vertebra and the second vertebra and being secured to each of the first vertebra and the second vertebra using an anterior approach. The plate 350 may have a front side 352 (which also may be referred to as an “anterior side” or a “first side”) and a back side (which also may be referred to as a “posterior side” or a “second side”) disposed opposite one another, a top end 356 (which also may be referred to as a “superior end” or a “first end”) and a bottom end 358 (which also may be referred to as an “inferior end” or a “second end”) disposed opposite one another, and a first lateral side 362 (which also may be referred to as a “third side”) and a second lateral side 364 (which also may be referred to as a “fourth side”) disposed opposite one another. As shown, the plate 350 may have a length $L_P$ between the top end 356 and the bottom end 358, a width $W_P$ between the first lateral side 362 and the second lateral side 364, and a thickness between the front side 352 and the back side.

In some embodiments, as shown, the plate 350 may include one or more openings configured for receiving the screws 390 therethrough and/or for allowing visualization of the cage 310 therethrough when the plate 350 is positioned over the cage 310 during a surgical procedure. According to the illustrated example, the plate 350 may include a plurality of screw openings 372 each extending from the front surface to the back surface of the plate 350 and configured for receiving one of the screws 390 therethrough for securing the plate 350 to the bone structures of the patient. As shown, the plate 350 may include a first pair of the screw openings 372 disposed near the top end 356 and a second pair of the screw openings 372 disposed near the bottom end 358. In some embodiments, the plate 350 also may include a central opening 374 extending from the front surface to the back surface of the plate 350 and configured for allowing visualization of the cage 310 therethrough when the plate 350 is positioned over the cage 310. As shown, the central opening 374 may be centered in the direction of the length $L_P$ of the plate 350 and in the direction of the width $W_P$ of the plate 350. In some embodiments, as shown, the plate 350 may include a pair of blocking members 376 that are rotatably coupled to the body of the plate 350 and configured for inhibiting the screws 390 from backing out of the bone structures after implantation. In particular, each of the blocking members 376 may be configured for rotating between an unblocked position, in which the blocking member 376 allows the screws 390 to be advanced through the adjacent screw openings 372 into the bone structures, and a blocked position, in which tabs of the blocking member 376 inhibit the screws 390 from backing out of the bone structures.

The plate 350 may include one or more plate alignment markings disposed on an exterior surface of the plate 350 and configured for being aligned with the one or more cage alignment markings of the cage 310. As shown, the plate 350 may include a first plate alignment marking 382*a* (which also may be referred to as a “first plate alignment line”), a second plate alignment marking 382*b* (which also may be referred to as a “second plate alignment line”), a third plate alignment marking 382*c* (which also may be referred to as a “third plate alignment line”), and a fourth plate alignment marking 382*d* (which also may be referred to as a “fourth plate alignment line”) disposed on the front surface of the plate 350. In some embodiments, as shown, the plate alignment markings 382*a*, 382*b*, 382*c*, 382*d* may be formed as lines or bands each extending in a linear manner. In some embodiments, as shown, the plate alignment markings 382*a*, 382*b*, 382*c*, 382*d* each may extend in the direction of the length $L_P$ of the plate 350. In some embodiments, as shown, the first plate alignment marking 182*a* and the second plate alignment marking 382*b* may be aligned with one another in the direction of the length $L_P$ of the plate 350, and the third plate alignment marking 382*c* and the fourth plate alignment marking 382*d* may be aligned with one another in the direction of the length $L_P$ of the plate 350. In some embodiments, as shown, the first plate alignment marking 182*a* and the second plate alignment marking 382*b* may be spaced apart from the third plate alignment marking 382*c* and the fourth plate alignment marking 382*d* on the front surface of the plate 350 in the direction of the width $W_P$ of the plate 350. In some embodiments, as shown, the central opening 374 may be disposed between the first plate alignment marking 382*a* and the second plate alignment marking 382*b* in the direction of the length $L_P$ of the plate 350, and the central opening 374 may be disposed between the third plate alignment marking 382*c* and the fourth plate alignment marking 382*d* in the direction of the length $L_P$ of the plate 350. In some embodiments, the plate alignment markings 382*a*, 382*b*, 382*c*, 382*d* may be laser markings, such as laser etched markings or laser engraved markings, although other suitable forms of the plate alignment markings 382*a*, 382*b*, 382*c*, 382*d* may be used in other embodiments. In some embodiments, the body of the plate 350 may be formed of titanium, although other suitable materials for the plate 350 may be used in other embodiments.

As mentioned above, the implantable construct 300 may be used for stabilizing a first bone structure and a second bone structure of a patient. In some embodiments, the first bone structure may be a first vertebra, and the second bone structure may be an adjacent second vertebra. During implantation of the construct 300, the cage 310 may be positioned between the first bone structure and the second bone structure. Then, the plate 350 may be positioned over the cage 310 and over respective portions of the first bone structure and the second bone structure. While positioning the plate 350, the cage alignment markings 342*a*, 342*b*, 342*c*, 342*d* and the plate alignment markings 382*a*, 382*b*, 382*c*, 382*d* may be used to align the plate 350 with the cage 310. In particular, the first plate alignment marking 382*a* and the second plate alignment marking 382*b* may be aligned with the first cage alignment marking 342*a* and the second cage alignment marking 342*b* in the direction of the height $H_C$ of the cage 310, and the third plate alignment marking 382*c* and the fourth plate alignment marking 382*d* may be aligned with the third cage alignment marking 342*c* and the fourth cage alignment marking 342*d* in the direction of the height $H_C$ of the cage 310, as shown in FIG. 3, such that the plate 350 is aligned with the cage 310. While maintaining such alignment of the plate 350 with the cage 310, the screws 390 may be advanced through the respective screw openings 372 and into the bone structures, thereby securing the plate 350 to each of the first bone structure and the second bone structure.

Figure 4:
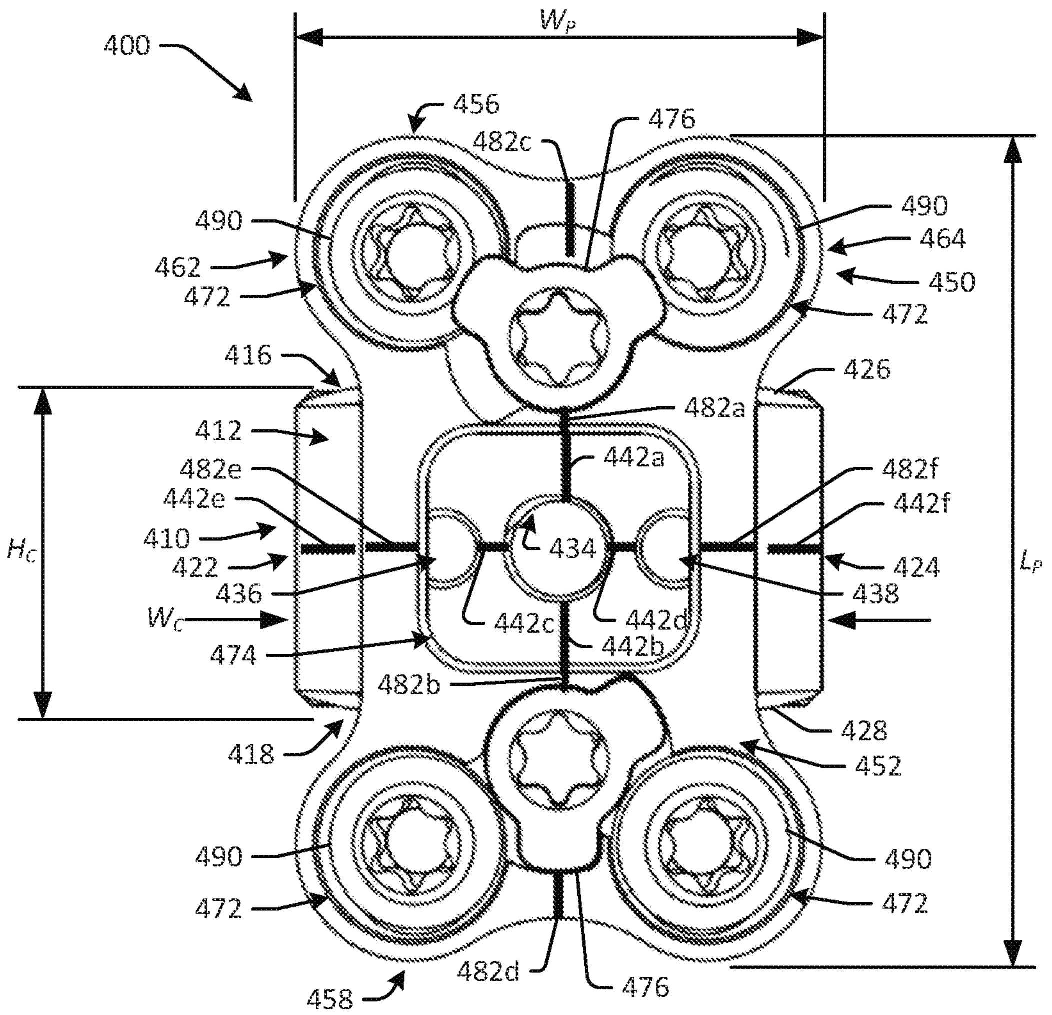
FIG. 4 is a perspective view of an example implantable construct in accordance with embodiments of the disclosure, showing a cage, a plate, and screws of the implantable construct.

FIG. 4 depicts another example implantable construct 400 in accordance with embodiments of the disclosure. As described below, the construct 400 may be implanted during a surgical procedure for stabilizing bone structures of a patient. In some embodiments, the construct 400 may be implanted during a spinal procedure for stabilizing adjacent vertebrae of a patient, although the construct 400 may be implanted during other types of surgical procedures for stabilizing bone structures of other portions of a patient's body. As shown, the construct 400 may include an implantable cage 410, an implantable plate 450, and a plurality of implantable screws 490. It will be appreciated that the illustrated configurations of the cage 410, the plate 450, and the screws 490 are merely examples, and that other configurations of the cage 410, the plate 450, and the screws 490 may be used in various embodiments. Certain similarities and differences between the construct 400 and the construct 100 will be appreciated from the drawings and the following description. Particular differences relate to configurations of cage alignment markings of the cage 410 and plate alignment markings of the plate 450.

The cage 410 (which also may be referred to as a "spinal cage," an "anterior spinal cage," an "interbody cage," or an "interbody device") may be configured for positioning between a first bone structure and a second bone structure of a patient. In some embodiments in which the construct 400 is used for a spinal procedure, the cage 410 may be configured for positioning between a first vertebra and an adjacent second vertebra (i.e., within the interbody space between the first vertebra and the second vertebra) of the patient. In some such embodiments, the cage 410 may be configured for positioning between the first vertebra and the second vertebra using an anterior approach. The cage 410 may have a front side 412 (which also may be referred to as an "anterior side" or a "first side") and a back side (which also may be referred to as a "posterior side" or a "second side") disposed opposite one another, a top side 416 (which also may be referred to as a "superior side" or a "third side") and a bottom side 418 (which also may be referred to as an "inferior side" or a "fourth side") disposed opposite one another, and a first lateral side 422 (which also may be referred to as a "fifth side") and a second lateral side 424 (which also may be referred to as a "sixth side") disposed opposite one another. As shown, the cage 410 may have a height $H_C$ between the top side 416 and the bottom side 418, a width $W_C$ between the first lateral side 422 and the second lateral side 424, and a depth between the front side 412 and the back side.

In some embodiments, as shown, the cage 410 may include one or more features configured for engaging the bone structures between which the cage 410 is positioned during use. According to the illustrated example, the cage 410 may include a plurality of first protrusions 426 disposed along the top side 416 of the cage 410 and configured for engaging the first bone structure and a plurality of second protrusions 428 disposed along the bottom side of the cage and configured for engaging the second bone structure. In some embodiments in which the construct 400 is used for a spinal procedure, the first protrusions 426 may be configured for engaging the superior vertebra, and the second protrusions 428 may be configured for engaging the inferior vertebra. In some embodiments, as shown, the first protrusions 426 and the second protrusions 428 may be formed as ribs extending in the direction of the width $W_C$ of the cage 410. Various other configurations and arrangements of the first protrusions 426 and the second protrusions 428 may be used in other embodiments.

In some embodiments, as shown, the cage 410 may include one or more openings configured for receiving and containing graft material therein and/or for facilitating engagement of the cage 410 with an instrument, such as an insertion instrument used for positioning the cage 410 between bone structures during a surgical procedure. According to the illustrated example, the cage 410 may include an internal opening extending from the top side 416 to the bottom side 418. The internal opening may be configured for receiving and containing graft material therein. In some embodiments, the cage 410 also may include a plurality of openings defined in the front surface of the cage 410 and extending from the front surface to the internal opening. As shown, the cage 410 may include a central opening 434 that is centered in the direction of the height $H_C$ of the cage 410 and in the direction of the width $W_C$ of the cage 410, a first lateral opening 436 that is centered in the direction of the height $H_C$ of the cage 410 and spaced apart from the central opening 434 toward the first lateral side 422 in the direction of the width $W_C$ of the cage 410, and a second lateral opening 438 that is that is centered in the direction of the height $H_C$ of the cage 410 and spaced apart from the central opening 434 toward the second lateral side 424 in the direction of the width $W_C$ of the cage 410. The central opening 434, the first lateral opening 436, and the second lateral opening 438 may be configured for receiving mating features of an insertion instrument during implantation of the cage. In some embodiments, the central opening 434 may be threaded, and the lateral openings 436, 438 may have smooth bores without threading, although other configurations of the central opening 434 and the lateral openings 436, 438 may be used in other embodiments.

The cage 410 may include one or more cage alignment markings disposed on an exterior surface of the cage 410 and configured for being aligned with one or more plate alignment markings of the plate 450, as described below. As shown, the cage 410 may include a first cage alignment marking 442*a* (which also may be referred to as a "first cage alignment line"), a second cage alignment marking 442*b* (which also may be referred to as a "second cage alignment line"), a third cage alignment marking 442*c* (which also may be referred to as a "third cage alignment line"), a fourth cage alignment marking 442*d* (which also may be referred to as a "fourth cage alignment line"), a fifth cage alignment marking 442*e* (which also may be referred to as a "fifth cage alignment line"), and a sixth cage alignment marking 442*f* (which also may be referred to as a "sixth cage alignment line") disposed on the front surface of the cage 410. In some embodiments, as shown, the cage alignment markings 442*a*, 442*b*, 442*c*, 442*d*, 442*e*, 442*f* may be formed as lines or bands each extending in a linear manner. In some embodiments, as shown, the first cage alignment marking 442*a* and the second cage alignment marking 442*b* each may extend in the direction of the height $H_C$ of the cage 410. In some embodiments, as shown, the first cage alignment marking 442*a* and the second cage alignment marking 442*b* may be aligned with one another in the direction of the height $H_C$ of the cage 410. In some embodiments, as shown, the first cage alignment marking 442*a* and the second cage alignment marking 442*b* may be centered on the front surface of the cage 410 in the direction of the width $W_C$ of the cage 410. In some embodiments, as shown, the central opening 434 may be disposed between the first cage alignment marking 442*a* and the second cage alignment marking 442*b* in the direction of the height $H_C$ of the cage 410. In some embodiments, as shown, the third cage alignment marking 442*c*, the fourth cage alignment marking 442*d*, the fifth cage alignment marking 442*e*, and the sixth cage alignment marking 442*f* each may extend in the direction of the width $W_C$ of the cage 410. In some embodiments, as shown, the third cage alignment marking 442*c*, the fourth cage alignment marking 442*d*, the fifth cage alignment marking 442*e*, and the sixth cage alignment marking 442*f* may be aligned with one another in the direction of the width $W_C$ of the cage 410. In some embodiments, as shown, the third cage alignment marking 442*c*, the fourth cage alignment marking 442*d*, the fifth cage alignment marking 442*e*, and the sixth cage alignment marking 442*f* may be centered on the front surface of the cage 410 in the direction of the height $H_C$ of the cage 410. In some embodiments, as shown, the central opening 434 may be disposed between the third cage alignment marking 442*c* and the fourth cage alignment marking 442*d* in the direction of the width $W_C$ of the cage 410, the first lateral opening 436 may be disposed between the third cage alignment marking 442*c* and the fifth cage alignment marking 442*e* in the direction of the width $W_C$ of the cage 410, and the second lateral opening 438 may be disposed between the fourth cage alignment marking 442*d* and the sixth cage alignment marking 442*f* in the direction of the width $W_C$ of the cage 410. In some embodiments, the cage alignment markings 442*a*, 442*b*, 442*c*, 442*d*, 442*e*, 442*f* may be laser markings, such as laser etched markings or laser engraved markings, although other suitable forms of the cage alignment markings 442*a*, 442*b*, 442*c*, 442*d*, 442*e*, 442*f* may be used in other embodiments. In some embodiments, the body of the cage 410 may be formed of polyether ether ketone (PEEK), although other suitable materials for the cage 410 may be used in other embodiments.

The plate 450 (which also may be referred to as a "spinal plate" or an "anterior spinal plate") may be configured for positioning over the cage 410 and respective portions of the first bone structure and the second bone structure and being secured to each of the first bone structure and the second bone structure by the screws 490. In some embodiments in which the construct 400 is used for a spinal procedure, the plate 450 may be configured for positioning over respective portions of the first vertebra and the second vertebra and being secured to each of the first vertebra and the second vertebra by the screws 490. In some such embodiments, the plate 450 may be configured for positioning over respective portions of the first vertebra and the second vertebra and being secured to each of the first vertebra and the second vertebra using an anterior approach. The plate 450 may have a front side 452 (which also may be referred to as an "anterior side" or a "first side") and a back side (which also may be referred to as a "posterior side" or a "second side") disposed opposite one another, a top end 456 (which also may be referred to as a "superior end" or a "first end") and a bottom end 458 (which also may be referred to as an "inferior end" or a "second end") disposed opposite one another, and a first lateral side 462 (which also may be referred to as a "third side") and a second lateral side 464 (which also may be referred to as a "fourth side") disposed opposite one another. As shown, the plate 450 may have a length $L_P$ between the top end 456 and the bottom end 458, a width $W_P$ between the first lateral side 462 and the second lateral side 464, and a thickness between the front side 452 and the back side.

In some embodiments, as shown, the plate 450 may include one or more openings configured for receiving the screws 490 therethrough and/or for allowing visualization of the cage 410 therethrough when the plate 450 is positioned over the cage 410 during a surgical procedure. According to the illustrated example, the plate 450 may include a plurality of screw openings 472 each extending from the front surface to the back surface of the plate 450 and configured for receiving one of the screws 490 therethrough for securing the plate 450 to the bone structures of the patient. As shown, the plate 450 may include a first pair of the screw openings 472 disposed near the top end 456 and a second pair of the screw openings 472 disposed near the bottom end 458. In some embodiments, the plate 450 also may include a central opening 474 extending from the front surface to the back surface of the plate 450 and configured for allowing visualization of the cage 410 therethrough when the plate 450 is positioned over the cage 410. As shown, the central opening 474 may be centered in the direction of the length $L_P$ of the plate 450 and in the direction of the width $W_P$ of the plate 450. In some embodiments, as shown, the plate 450 may include a pair of blocking members 476 that are rotatably coupled to the body of the plate 450 and configured for inhibiting the screws 490 from backing out of the bone structures after implantation. In particular, each of the blocking members 476 may be configured for rotating between an unblocked position, in which the blocking member 476 allows the screws 490 to be advanced through the adjacent screw openings 472 into the bone structures, and a blocked position, in which tabs of the blocking member 476 inhibit the screws 490 from backing out of the bone structures.

The plate 450 may include one or more plate alignment markings disposed on an exterior surface of the plate 450 and configured for being aligned with the one or more cage alignment markings of the cage 410. As shown, the plate 450 may include a first plate alignment marking 482*a* (which also may be referred to as a "first plate alignment line"), a second plate alignment marking 482*b* (which also may be referred to as a "second plate alignment line"), a third plate alignment marking 482*c* (which also may be referred to as a "third plate alignment line"), a fourth plate alignment marking 482*d* (which also may be referred to as a "fourth plate alignment line"), a fifth plate alignment marking 482*e* (which also may be referred to as a "fifth plate alignment line"), and a sixth plate alignment marking 482*f* (which also may be referred to as a "sixth plate alignment line") disposed on the front surface of the plate 250. In some embodiments, as shown, the plate alignment markings 482*a*, 482*b*, 482*c*, 482*d*, 482*e*, 482*f* may be formed as lines or bands each extending in a linear manner. In some embodiments, as shown, the first plate alignment marking 482*a*, the second plate alignment marking 482*b*, the third plate alignment marking 482*c*, and the fourth plate alignment marking 482*d* each may extend in the direction of the length $L_P$ of the plate 450. In some embodiments, as shown, the first plate alignment marking 482*a*, the second plate alignment marking 482*b*, the third plate alignment marking 482*c*, and the fourth plate alignment marking 482*d* may be aligned with one another in the direction of the length $L_P$ of the plate 450. In some embodiments, as shown, the first plate alignment marking 482*a*, the second plate alignment marking 482*b*, the third plate alignment marking 482*c*, and the fourth plate alignment marking 482*d* may be centered on the front surface of the plate 450 in the direction of the width $W_P$ of the plate 450. In some embodiments, as shown, the central opening 474 may be disposed between the first plate alignment marking 482*a* and the second plate alignment marking 482*b* in the direction of the length $L_P$ of the plate 450. In some embodiments, as shown, one of the blocking members 476 may be disposed between the first plate alignment marking 482*a* and the third plate alignment marking 482*c* in the direction of the length $L_P$ of the plate 450, and the other blocking member 476 may be disposed between the second plate alignment marking 482*b* and the fourth plate alignment marking 482*d* in the direction of the length $L_P$ of the plate 450. In some embodiments, as shown, the fifth plate alignment marking 482*e* and the sixth plate alignment marking 482*f* each may extend in the direction of the width $W_P$ of the plate 450. In some embodiments, as shown, the fifth plate alignment marking 482*e* and the sixth plate alignment marking 482*f* may be aligned with one another in the direction of the width $W_P$ of the plate 450. In some embodiments, as shown, the fifth plate alignment marking 482*e* and the sixth plate alignment marking 482*f* may be centered on the front surface of the plate 450 in the direction of the length $L_P$ of the plate 450. In some embodiments, as shown, the central opening 474 may be disposed between the fifth plate alignment marking 482*e* and the sixth plate alignment marking 482*f* in the direction of the width $W_P$ of the plate 450. In some embodiments, the plate alignment markings 482*a*, 482*b*, 482*c*, 482*d*, 482*e*, 482*f* may be laser markings, such as laser etched markings or laser engraved markings, although other suitable forms of the plate alignment markings 482*a*, 482*b*, 482*c*, 482*d*, 482*e*, 482*f* may be used in other embodiments. In some embodiments, the body of the plate 450 may be formed of titanium, although other suitable materials for the plate 450 may be used in other embodiments.

As mentioned above, the implantable construct 400 may be used for stabilizing a first bone structure and a second bone structure of a patient. In some embodiments, the first bone structure may be a first vertebra, and the second bone structure may be an adjacent second vertebra. During implantation of the construct 400, the cage 410 may be positioned between the first bone structure and the second bone structure. Then, the plate 450 may be positioned over the cage 410 and over respective portions of the first bone structure and the second bone structure. While positioning the plate 450, the cage alignment markings 442*a*, 442*b*, 442*c*, 442*d*, 442*e*, 442*f* and the plate alignment markings 482*a*, 482*b*, 482*c*, 482*d*, 482*e*, 482*f* may be used to align the plate 450 with the cage 410. In particular, the first plate alignment marking 482*a*, the second plate alignment marking 482*b*, the third plate alignment marking 482*c*, and the fourth plate alignment marking 482*d* may be aligned with the first cage alignment marking 442*a* and the second cage alignment marking 442*b* in the direction of the height $H_C$ of the cage 410, while the fifth plate alignment marking 482*e* and the sixth plate alignment marking 482*f* may be aligned with the third cage alignment marking 442*c*, the fourth cage alignment marking 442*d*, the fifth cage alignment marking 442*e*, and the sixth cage alignment marking 442*f* in the direction of the width $W_C$ of the cage 410, as shown in FIG. 4, such that the plate 450 is aligned with the cage 410. While maintaining such alignment of the plate 450 with the cage 410, the screws 490 may be advanced through the respective screw openings 472 and into the bone structures, thereby securing the plate 450 to each of the first bone structure and the second bone structure.

Figure 5:
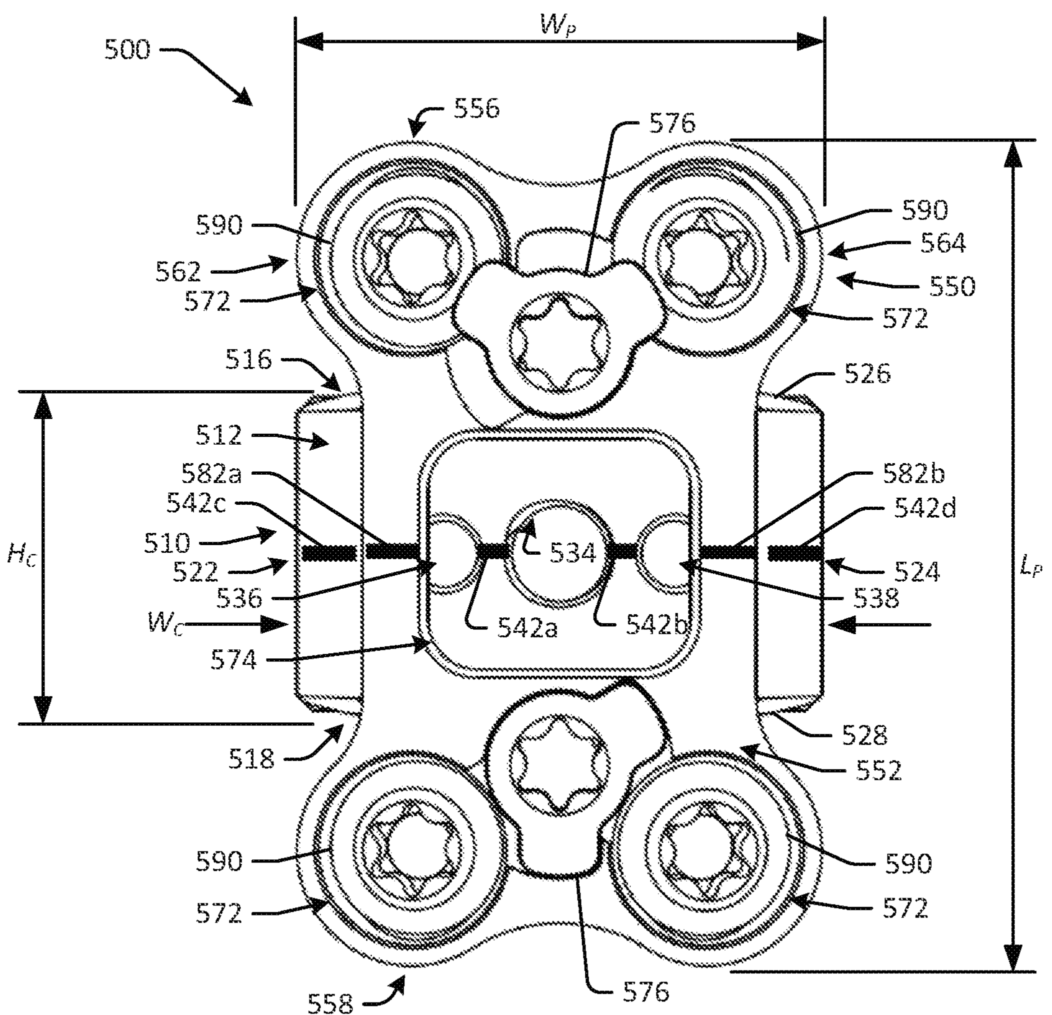
FIG. 5 is a perspective view of an example implantable construct in accordance with embodiments of the disclosure, showing a cage, a plate, and screws of the implantable construct.

FIG. 5 depicts another example implantable construct 500 in accordance with embodiments of the disclosure. As described below, the construct 500 may be implanted during a surgical procedure for stabilizing bone structures of a patient. In some embodiments, the construct 500 may be implanted during a spinal procedure for stabilizing adjacent vertebrae of a patient, although the construct 500 may be implanted during other types of surgical procedures for stabilizing bone structures of other portions of a patient's body. As shown, the construct 500 may include an implantable cage 510, an implantable plate 550, and a plurality of implantable screws 590. It will be appreciated that the illustrated configurations of the cage 510, the plate 550, and the screws 590 are merely examples, and that other configurations of the cage 510, the plate 550, and the screws 590 may be used in various embodiments. Certain similarities and differences between the construct 500 and the construct 100 will be appreciated from the drawings and the following description. Particular differences relate to configurations of cage alignment markings of the cage 510 and plate alignment markings of the plate 550.

The cage 510 (which also may be referred to as a "spinal cage," an "anterior spinal cage," an "interbody cage," or an "interbody device") may be configured for positioning between a first bone structure and a second bone structure of a patient. In some embodiments in which the construct 500 is used for a spinal procedure, the cage 510 may be configured for positioning between a first vertebra and an adjacent second vertebra (i.e., within the interbody space between the first vertebra and the second vertebra) of the patient. In some such embodiments, the cage 510 may be configured for positioning between the first vertebra and the second vertebra using an anterior approach. The cage 510 may have a front side 512 (which also may be referred to as an "anterior side" or a "first side") and a back side (which also may be referred to as a "posterior side" or a "second side") disposed opposite one another, a top side 516 (which also may be referred to as a "superior side" or a "third side") and a bottom side 518 (which also may be referred to as an "inferior side" or a "fourth side") disposed opposite one another, and a first lateral side 522 (which also may be referred to as a "fifth side") and a second lateral side 524 (which also may be referred to as a "sixth side") disposed opposite one another. As shown, the cage 510 may have a height $H_C$ between the top side 516 and the bottom side 518, a width $W_C$ between the first lateral side 522 and the second lateral side 524, and a depth between the front side 512 and the back side.

In some embodiments, as shown, the cage 510 may include one or more features configured for engaging the bone structures between which the cage 510 is positioned during use. According to the illustrated example, the cage 510 may include a plurality of first protrusions 526 disposed along the top side 516 of the cage 510 and configured for engaging the first bone structure and a plurality of second protrusions 528 disposed along the bottom side of the cage and configured for engaging the second bone structure. In some embodiments in which the construct 500 is used for a spinal procedure, the first protrusions 526 may be configured for engaging the superior vertebra, and the second protrusions 528 may be configured for engaging the inferior vertebra. In some embodiments, as shown, the first protrusions 526 and the second protrusions 528 may be formed as ribs extending in the direction of the width $W_C$ of the cage 510. Various other configurations and arrangements of the first protrusions 526 and the second protrusions 528 may be used in other embodiments.

In some embodiments, as shown, the cage 510 may include one or more openings configured for receiving and containing graft material therein and/or for facilitating engagement of the cage 510 with an instrument, such as an insertion instrument used for positioning the cage 510 between bone structures during a surgical procedure. According to the illustrated example, the cage 510 may include an internal opening extending from the top side 516 to the bottom side 518. The internal opening may be configured for receiving and containing graft material therein. In some embodiments, the cage 510 also may include a plurality of openings defined in the front surface of the cage 510 and extending from the front surface to the internal opening. As shown, the cage 510 may include a central opening 534 that is centered in the direction of the height $H_C$ of the cage 510 and in the direction of the width $W_C$ of the cage 510, a first lateral opening 536 that is centered in the direction of the height $H_C$ of the cage 510 and spaced apart from the central opening 534 toward the first lateral side 522 in the direction of the width $W_C$ of the cage 510, and a second lateral opening 538 that is that is centered in the direction of the height $H_C$ of the cage 510 and spaced apart from the central opening 534 toward the second lateral side 524 in the direction of the width $W_C$ of the cage 510. The central opening 534, the first lateral opening 536, and the second lateral opening 538 may be configured for receiving mating features of an insertion instrument during implantation of the cage. In some embodiments, the central opening 534 may be threaded, and the lateral openings 536, 538 may have smooth bores without threading, although other configurations of the central opening 534 and the lateral openings 536, 538 may be used in other embodiments.

The cage 510 may include one or more cage alignment markings disposed on an exterior surface of the cage 510 and configured for being aligned with one or more plate alignment markings of the plate 550, as described below. As shown, the cage 510 may include a first cage alignment marking 542*a* (which also may be referred to as a "first cage alignment line"), a second cage alignment marking 542*b* (which also may be referred to as a "second cage alignment line"), a third cage alignment marking 542*c* (which also may be referred to as a "third cage alignment line"), and a fourth cage alignment marking 542*d* (which also may be referred to as a "fourth cage alignment line") disposed on the front surface of the cage 510. In some embodiments, as shown, the cage alignment markings 542*a*, 542*b*, 542*c*, 542*d* may be formed as lines or bands each extending in a linear manner. In some embodiments, as shown, the cage alignment markings 542*a*, 542*b*, 542*c*, 542*d* each may extend in the direction of the width $W_C$ of the cage 510. In some embodiments, as shown, the cage alignment markings 542*a*, 542*b*, 542*c*, 542*d* may be aligned with one another in the direction of the width $W_C$ of the cage 510. In some embodiments, as shown, the cage alignment markings 542*a*, 542*b*, 542*c*, 542*d* may be centered on the front surface of the cage 510 in the direction of the height $H_C$ of the cage 510. In some embodiments, as shown, the central opening 534 may be disposed between the first cage alignment marking 542*a* and the second cage alignment marking 542*b* in the direction of the width $W_C$ of the cage 510, the first lateral opening 536 may be disposed between the first cage alignment marking 542*a* and the third cage alignment marking 542*c* in the direction of the width $W_C$ of the cage 510, and the second lateral opening 538 may be disposed between the second cage alignment marking 542*b* and the fourth cage alignment marking 542*d* in the direction of the width $W_C$ of the cage 510. In some embodiments, the cage alignment markings 542*a*, 542*b*, 542*c*, 542*d* may be laser markings, such as laser etched markings or laser engraved markings, although other suitable forms of the cage alignment markings 542*a*, 542*b*, 542*c*, 542*d* may be used in other embodiments. In some embodiments, the body of the cage 510 may be formed of polyether ether ketone (PEEK), although other suitable materials for the cage 510 may be used in other embodiments.

The plate 550 (which also may be referred to as a "spinal plate" or an "anterior spinal plate") may be configured for positioning over the cage 510 and respective portions of the first bone structure and the second bone structure and being secured to each of the first bone structure and the second bone structure by the screws 590. In some embodiments in which the construct 500 is used for a spinal procedure, the plate 550 may be configured for positioning over respective portions of the first vertebra and the second vertebra and being secured to each of the first vertebra and the second vertebra by the screws 590. In some such embodiments, the plate 550 may be configured for positioning over respective portions of the first vertebra and the second vertebra and being secured to each of the first vertebra and the second vertebra using an anterior approach. The plate 550 may have a front side 552 (which also may be referred to as an "anterior side" or a "first side") and a back side (which also may be referred to as a "posterior side" or a "second side") disposed opposite one another, a top end 556 (which also may be referred to as a "superior end" or a "first end") and a bottom end 558 (which also may be referred to as an "inferior end" or a "second end") disposed opposite one another, and a first lateral side 562 (which also may be referred to as a "third side") and a second lateral side 564 (which also may be referred to as a "fourth side") disposed opposite one another. As shown, the plate 550 may have a length $L_P$ between the top end 556 and the bottom end 558, a width $W_P$ between the first lateral side 562 and the second lateral side 564, and a thickness between the front side 552 and the back side.

In some embodiments, as shown, the plate 550 may include one or more openings configured for receiving the screws 590 therethrough and/or for allowing visualization of the cage 510 therethrough when the plate 550 is positioned over the cage 510 during a surgical procedure. According to the illustrated example, the plate 550 may include a plurality of screw openings 572 each extending from the front surface to the back surface of the plate 550 and configured for receiving one of the screws 590 therethrough for securing the plate 550 to the bone structures of the patient. As shown, the plate 550 may include a first pair of the screw openings 572 disposed near the top end 556 and a second pair of the screw openings 572 disposed near the bottom end 558. In some embodiments, the plate 550 also may include a central opening 574 extending from the front surface to the back surface of the plate 550 and configured for allowing visualization of the cage 510 therethrough when the plate 550 is positioned over the cage 510. As shown, the central opening 574 may be centered in the direction of the length $L_P$ of the plate 550 and in the direction of the width $W_P$ of the plate 550. In some embodiments, as shown, the plate 550 may include a pair of blocking members 576 that are rotatably coupled to the body of the plate 550 and configured for inhibiting the screws 590 from backing out of the bone structures after implantation. In particular, each of the blocking members 576 may be configured for rotating between an unblocked position, in which the blocking member 576 allows the screws 590 to be advanced through the adjacent screw openings 572 into the bone structures, and a blocked position, in which tabs of the blocking member 576 inhibit the screws 590 from backing out of the bone structures.

The plate 550 may include one or more plate alignment markings disposed on an exterior surface of the plate 550 and configured for being aligned with the one or more cage alignment markings of the cage 510. As shown, the plate 550 may include a first plate alignment marking 582*a* (which also may be referred to as a "first plate alignment line") and a second plate alignment marking 582*b* (which also may be referred to as a "second plate alignment line") disposed on the front surface of the plate 550. In some embodiments, as shown, the plate alignment markings 582*a*, 582*b* may be formed as lines or bands each extending in a linear manner. In some embodiments, as shown, the plate alignment markings 582*a*, 582*b* each may extend in the direction of the width $W_P$ of the plate 550. In some embodiments, as shown, the plate alignment markings 582*a*, 582*b* may be aligned with one another in the direction of the width $W_P$ of the plate 550. In some embodiments, as shown, the plate alignment markings 582*a*, 582*b* may be centered on the front surface of the plate 550 in the direction of the length $L_P$ of the plate 550. In some embodiments, as shown, the central opening 574 may be disposed between the first plate alignment marking 582*a* and the second plate alignment marking 582*b* in the direction of the width $W_P$ of the plate 550. In some embodiments, the plate alignment markings 582*a*, 582*b* may be laser markings, such as laser etched markings or laser engraved markings, although other suitable forms of the plate alignment markings 582*a*, 582*b* may be used in other embodiments. In some embodiments, the body of the plate 550 may be formed of titanium, although other suitable materials for the plate 550 may be used in other embodiments.

As mentioned above, the implantable construct 500 may be used for stabilizing a first bone structure and a second bone structure of a patient. In some embodiments, the first bone structure may be a first vertebra, and the second bone structure may be an adjacent second vertebra. During implantation of the construct 500, the cage 510 may be positioned between the first bone structure and the second bone structure. Then, the plate 550 may be positioned over the cage 510 and over respective portions of the first bone structure and the second bone structure. While positioning the plate 550, the cage alignment markings 542*a*, 542*b*, 542*c*, 542*d* and the plate alignment markings 582*a*, 582*b* may be used to align the plate 550 with the cage 510. In particular, the plate alignment markings 582*a*, 582*b* may be aligned with the cage alignment markings 542*a*, 542*b*, 542*c*, 542*d* in the direction of the width $W_C$ of the cage 510, as shown in FIG. 5, such that the plate 550 is aligned with the cage 510. While maintaining such alignment of the plate 550 with the cage 510, the screws 590 may be advanced through the respective screw openings 572 and into the bone structures, thereby securing the plate 550 to each of the first bone structure and the second bone structure.

Figure 6:
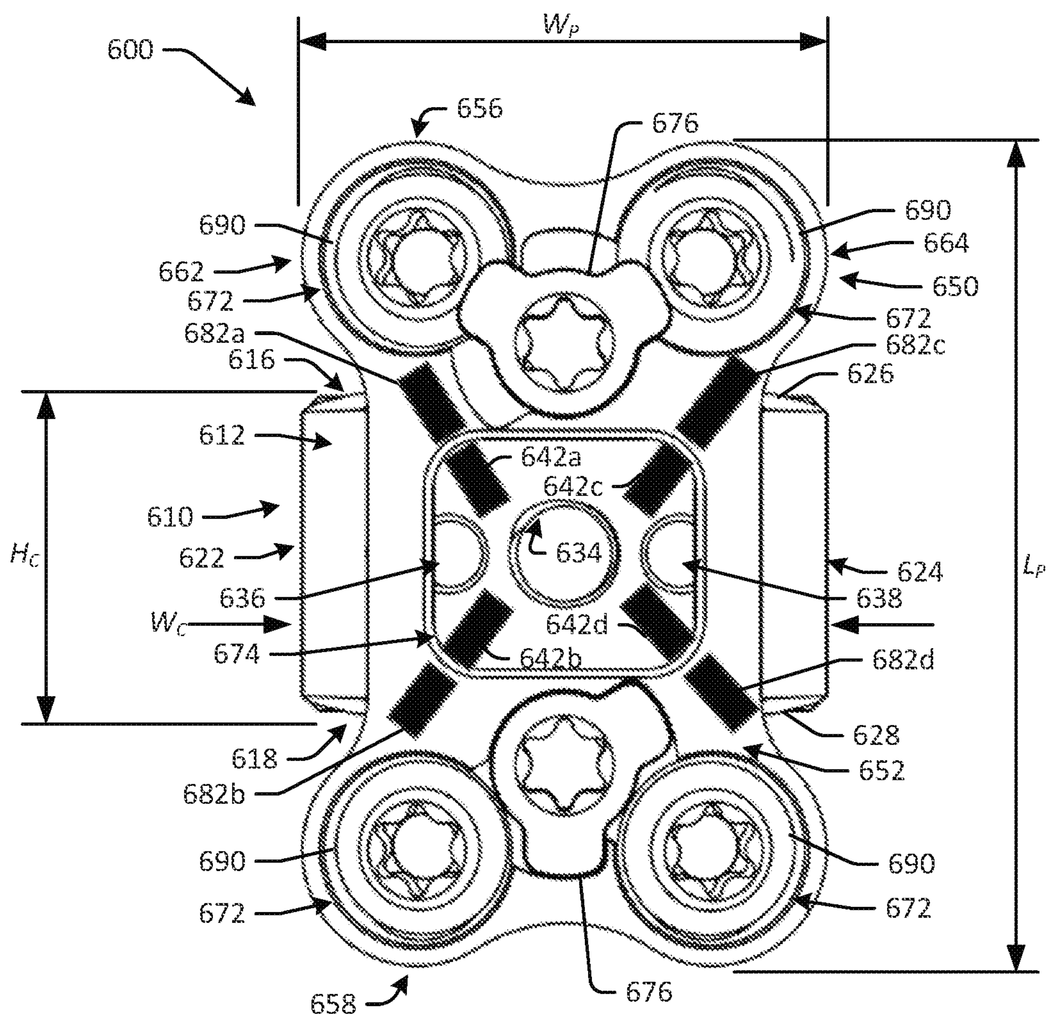
FIG. 6 is a perspective view of an example implantable construct in accordance with embodiments of the disclosure, showing a cage, a plate, and screws of the implantable construct.

FIG. 6 depicts another example implantable construct 600 in accordance with embodiments of the disclosure. As described below, the construct 600 may be implanted during a surgical procedure for stabilizing bone structures of a patient. In some embodiments, the construct 600 may be implanted during a spinal procedure for stabilizing adjacent vertebrae of a patient, although the construct 600 may be implanted during other types of surgical procedures for stabilizing bone structures of other portions of a patient's body. As shown, the construct 600 may include an implantable cage 610, an implantable plate 650, and a plurality of implantable screws 690. It will be appreciated that the illustrated configurations of the cage 510, the plate 650, and the screws 690 are merely examples, and that other configurations of the cage 610, the plate 650, and the screws 690 may be used in various embodiments. Certain similarities and differences between the construct 600 and the construct 100 will be appreciated from the drawings and the following description. Particular differences relate to configurations of cage alignment markings of the cage 610 and plate alignment markings of the plate 650.

The cage 610 (which also may be referred to as a "spinal cage," an "anterior spinal cage," an "interbody cage," or an "interbody device") may be configured for positioning between a first bone structure and a second bone structure of a patient. In some embodiments in which the construct 600 is used for a spinal procedure, the cage 610 may be configured for positioning between a first vertebra and an adjacent second vertebra (i.e., within the interbody space between the first vertebra and the second vertebra) of the patient. In some such embodiments, the cage 610 may be configured for positioning between the first vertebra and the second vertebra using an anterior approach. The cage 610 may have a front side 612 (which also may be referred to as an "anterior side" or a "first side") and a back side (which also may be referred to as a "posterior side" or a "second side") disposed opposite one another, a top side 616 (which also may be referred to as a "superior side" or a "third side") and a bottom side 618 (which also may be referred to as an "inferior side" or a "fourth side") disposed opposite one another, and a first lateral side 622 (which also may be referred to as a "fifth side") and a second lateral side 624 (which also may be referred to as a "sixth side") disposed opposite one another. As shown, the cage 610 may have a height $H_C$ between the top side 616 and the bottom side 618, a width $W_C$ between the first lateral side 622 and the second lateral side 624, and a depth between the front side 612 and the back side.

In some embodiments, as shown, the cage 610 may include one or more features configured for engaging the bone structures between which the cage 610 is positioned during use. According to the illustrated example, the cage 610 may include a plurality of first protrusions 626 disposed along the top side 616 of the cage 610 and configured for engaging the first bone structure and a plurality of second protrusions 628 disposed along the bottom side of the cage and configured for engaging the second bone structure. In some embodiments in which the construct 600 is used for a spinal procedure, the first protrusions 626 may be configured for engaging the superior vertebra, and the second protrusions 628 may be configured for engaging the inferior vertebra. In some embodiments, as shown, the first protrusions 626 and the second protrusions 628 may be formed as ribs extending in the direction of the width $W_C$ of the cage 610. Various other configurations and arrangements of the first protrusions 626 and the second protrusions 628 may be used in other embodiments.

In some embodiments, as shown, the cage 610 may include one or more openings configured for receiving and containing graft material therein and/or for facilitating engagement of the cage 610 with an instrument, such as an insertion instrument used for positioning the cage 610 between bone structures during a surgical procedure. According to the illustrated example, the cage 610 may include an internal opening extending from the top side 616 to the bottom side 618. The internal opening may be configured for receiving and containing graft material therein. In some embodiments, the cage 610 also may include a plurality of openings defined in the front surface of the cage 610 and extending from the front surface to the internal opening. As shown, the cage 610 may include a central opening 634 that is centered in the direction of the height $H_C$ of the cage 610 and in the direction of the width $W_C$ of the cage 610, a first lateral opening 636 that is centered in the direction of the height $H_C$ of the cage 610 and spaced apart from the central opening 634 toward the first lateral side 622 in the direction of the width $W_C$ of the cage 610, and a second lateral opening 638 that is that is centered in the direction of the height $H_C$ of the cage 610 and spaced apart from the central opening 634 toward the second lateral side 624 in the direction of the width $W_C$ of the cage 610. The central opening 634, the first lateral opening 636, and the second lateral opening 638 may be configured for receiving mating features of an insertion instrument during implantation of the cage. In some embodiments, the central opening 634 may be threaded, and the lateral openings 636, 638 may have smooth bores without threading, although other configurations of the central opening 634 and the lateral openings 636, 638 may be used in other embodiments.

The cage 610 may include one or more cage alignment markings disposed on an exterior surface of the cage 610 and configured for being aligned with one or more plate alignment markings of the plate 650, as described below. As shown, the cage 610 may include a first cage alignment marking 642*a* (which also may be referred to as a "first cage alignment line"), a second cage alignment marking 642*b* (which also may be referred to as a "second cage alignment line"), a third cage alignment marking 642*c* (which also may be referred to as a "third cage alignment line"), and a fourth cage alignment marking 642*d* (which also may be referred to as a "fourth cage alignment line") disposed on the front surface of the cage 610. In some embodiments, as shown, the cage alignment markings 642*a*, 642*b*, 642*c*, 642*d* may be formed as lines or bands each extending in a linear manner. In some embodiments, as shown, the first cage alignment marking 642*a* may extend in a first direction transverse to each of the height $H_C$ and the width $W_C$ of the cage 610, the second cage alignment marking 642*b* may extend in a second direction transverse to each of the height $H_C$ and the width $W_C$ of the cage 610, the third cage alignment marking 642*c* may extend in a third direction transverse to each of the height $H_C$ and the width $W_C$ of the cage 610, and the fourth cage alignment marking 642*d* may extend in a fourth direction transverse to each of the height $H_C$ and the width $W_C$ of the cage 610. In some embodiments, as shown, the first cage alignment marking 642*a* and the fourth cage alignment marking 642*d* may extend parallel to one another, and the second cage alignment marking 642*b* and the third cage alignment marking 642*c* may extend parallel to one another. In some embodiments, the cage alignment markings 642*a*, 642*b*, 642*c*, 642*d* may be laser markings, such as laser etched markings or laser engraved markings, although other suitable forms of the cage alignment markings 642*a*, 642*b*, 642*c*, 642*d* may be used in other embodiments. In some embodiments, the body of the cage 610 may be formed of polyether ether ketone (PEEK), although other suitable materials for the cage 610 may be used in other embodiments.

The plate 650 (which also may be referred to as a "spinal plate" or an "anterior spinal plate") may be configured for positioning over the cage 610 and respective portions of the first bone structure and the second bone structure and being secured to each of the first bone structure and the second bone structure by the screws 690. In some embodiments in which the construct 600 is used for a spinal procedure, the plate 650 may be configured for positioning over respective portions of the first vertebra and the second vertebra and being secured to each of the first vertebra and the second vertebra by the screws 690. In some such embodiments, the plate 650 may be configured for positioning over respective portions of the first vertebra and the second vertebra and being secured to each of the first vertebra and the second vertebra using an anterior approach. The plate 650 may have a front side 652 (which also may be referred to as an "anterior side" or a "first side") and a back side (which also may be referred to as a "posterior side" or a "second side") disposed opposite one another, a top end 656 (which also may be referred to as a "superior end" or a "first end") and a bottom end 658 (which also may be referred to as an "inferior end" or a "second end") disposed opposite one another, and a first lateral side 662 (which also may be referred to as a "third side") and a second lateral side 664 (which also may be referred to as a "fourth side") disposed opposite one another. As shown, the plate 650 may have a length $L_P$ between the top end 656 and the bottom end 658, a width $W_P$ between the first lateral side 662 and the second lateral side 664, and a thickness between the front side 652 and the back side.

In some embodiments, as shown, the plate 650 may include one or more openings configured for receiving the screws 690 therethrough and/or for allowing visualization of the cage 610 therethrough when the plate 650 is positioned over the cage 610 during a surgical procedure. According to the illustrated example, the plate 650 may include a plurality of screw openings 672 each extending from the front surface to the back surface of the plate 650 and configured for receiving one of the screws 690 therethrough for securing the plate 650 to the bone structures of the patient. As shown, the plate 650 may include a first pair of the screw openings 672 disposed near the top end 656 and a second pair of the screw openings 672 disposed near the bottom end 658. In some embodiments, the plate 650 also may include a central opening 674 extending from the front surface to the back surface of the plate 650 and configured for allowing visualization of the cage 610 therethrough when the plate 650 is positioned over the cage 610. As shown, the central opening 674 may be centered in the direction of the length $L_P$ of the plate 650 and in the direction of the width $W_P$ of the plate 650. In some embodiments, as shown, the plate 650 may include a pair of blocking members 676 that are rotatably coupled to the body of the plate 650 and configured for inhibiting the screws 690 from backing out of the bone structures after implantation. In particular, each of the blocking members 676 may be configured for rotating between an unblocked position, in which the blocking member 676 allows the screws 690 to be advanced through the adjacent screw openings 672 into the bone structures, and a blocked position, in which tabs of the blocking member 676 inhibit the screws 690 from backing out of the bone structures.

The plate 650 may include one or more plate alignment markings disposed on an exterior surface of the plate 650 and configured for being aligned with the one or more cage alignment markings of the cage 610. As shown, the plate 650 may include a first plate alignment marking 682*a* (which also may be referred to as a "first plate alignment line"), a second plate alignment marking 682*b* (which also may be referred to as a "second plate alignment line"), a third plate alignment marking 682*c* (which also may be referred to as a "third plate alignment line"), and a fourth plate alignment marking 682*d* (which also may be referred to as a "fourth plate alignment line") disposed on the front surface of the plate 650. In some embodiments, as shown, the plate alignment markings 682*a*, 682*b*, 682*c*, 682*d* may be formed as lines or bands each extending in a linear manner. In some embodiments, as shown, the first plate alignment marking 682*a* may extend in a first direction transverse to each of the length $L_P$ and the width $W_P$ of the plate 650, the second plate alignment marking 682*b* may extend in a second direction transverse to each of the length $L_P$ and the width $W_P$ of the plate 650, the third plate alignment marking 682*c* may extend in a third direction transverse to each of the length $L_P$ and the width $W_P$ of the plate 650, and the fourth plate alignment marking 682*d* may extend in a fourth direction transverse to each of the length $L_P$ and the width $W_P$ of the plate 650. In some embodiments, as shown, the first plate alignment marking 682*a* and the fourth plate alignment marking 682*d* may extend parallel to one another, and the second plate alignment marking 682*b* and the third plate alignment marking 682*c* may extend parallel to one another. In some embodiments, the plate alignment markings 682*a*, 682*b*, 682*c*, 682*d* may be laser markings, such as laser etched markings or laser engraved markings, although other suitable forms of the plate alignment markings 682*a*, 682*b*, 682*c*, 682*d* may be used in other embodiments. In some embodiments, the body of the plate 650 may be formed of titanium, although other suitable materials for the plate 650 may be used in other embodiments.

As mentioned above, the implantable construct 600 may be used for stabilizing a first bone structure and a second bone structure of a patient. In some embodiments, the first bone structure may be a first vertebra, and the second bone structure may be an adjacent second vertebra. During implantation of the construct 600, the cage 610 may be positioned between the first bone structure and the second bone structure. Then, the plate 650 may be positioned over the cage 610 and over respective portions of the first bone structure and the second bone structure. While positioning the plate 650, the cage alignment markings 642*a*, 642*b*, 642*c*, 642*d* and the plate alignment markings 682*a*, 682*b*, 682*c*, 682*d* may be used to align the plate 650 with the cage 610. In particular, the first plate alignment marking 682*a* may be aligned with the first cage alignment marking 642*a*, the second plate alignment marking 682*b* may be aligned with the second cage alignment marking 642*b*, the third plate alignment marking 682*c* may be aligned with the third cage alignment marking 642*c*, and the fourth plate alignment marking 682*d* may be aligned with the fourth cage alignment marking 642*d*, as shown in FIG. 6, such that the plate 650 is aligned with the cage 610. While maintaining such alignment of the plate 650 with the cage 610, the screws 690 may be advanced through the respective screw openings 672 and into the bone structures, thereby securing the plate 650 to each of the first bone structure and the second bone structure.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. An implantable construct for stabilizing a first bone structure and a second bone structure of a patient, the implantable construct comprising:

a cage configured for positioning between the first bone structure and the second bone structure, the cage comprising one or more cage alignment markings disposed on an exterior surface of the cage, where the one or more cage alignment markings comprises a cage alignment marking extending in a direction of a width of the cage between a medial side edge and a lateral side edge of the cage, and a cage alignment marking extending in a direction of a height of the cage between an upper side edge and a lower side edge of the cage; and a plate configured for positioning over the cage and being secured to each of the first bone structure and the second bone structure, the plate comprising one or more plate alignment markings disposed on an exterior surface of the plate, where the one or more plate alignment markings comprise a plate alignment marking extending in a direction of a width of the plate between a medial side edge and a lateral side edge of the plate, and a plate alignment marking extending between an upper side edge and a lower side edge of the plate, wherein the one or more plate alignment markings of the plate are configured for being aligned with the one or more cage alignment markings such that the plate is aligned with the cage.

2. The implantable construct of claim 1, wherein the width of the cage extends perpendicular to the height of the cage, wherein the one or more cage alignment markings comprises one or more cage alignment lines extending in the direction of the height of the cage, wherein the width of the plate extends perpendicular to a length of the plate, and wherein the one or more plate alignment markings comprises one or more plate alignment lines extending in the direction of the length of the plate extend between the upper side edge and the lower side edge of the plate, wherein the one or more plate alignment lines are configured for being aligned with the one or more cage alignment lines in the direction of the height of the cage such that the plate is aligned with the cage.

3. The implantable construct of claim 2, wherein the one or more cage alignment lines comprises a first cage alignment line and a second cage alignment line, and wherein the one or more plate alignment lines comprises a first plate alignment line and a second plate alignment line.

4. The implantable construct of claim 3, wherein the first cage alignment line and the second cage alignment line are aligned with one another in the direction of the height of the cage, and wherein the first plate alignment line and the second plate alignment line are aligned with one another in the direction of the length of the plate.

5. The implantable construct of claim 4, wherein the cage comprises a cage opening defined in the exterior surface of the cage and disposed between the first cage alignment line and the second cage alignment line in the direction of the height of the cage, and wherein the plate comprises a plate opening defined in the exterior surface of the plate and disposed between the first plate alignment line and the second plate alignment line in the direction of the length of the plate.

6. The implantable construct of claim 3, wherein the first cage alignment line and the second cage alignment line are spaced apart from one another in the direction of the width of the cage, and wherein the first plate alignment line and the second plate alignment line are spaced apart from one another in the direction of the width of the plate.

7. The implantable construct of claim 1, wherein the width of the cage extends perpendicular to the height of the cage, wherein the one or more cage alignment markings comprises one or more cage alignment lines extending in the direction of the width of the cage, wherein the width of the plate extends perpendicular to a length of the plate, and wherein the one or more plate alignment markings comprises one or more plate alignment lines extending in the direction of the width of the plate.

8. The implantable construct of claim 7, wherein the one or more cage alignment lines comprises a first cage alignment line and a second cage alignment line, and wherein the one or more plate alignment lines comprises a first plate alignment line and a second plate alignment line, wherein the first cage alignment line and the second cage alignment line are aligned with one another in the direction of the width of the cage, and wherein the first plate alignment line and the second plate alignment line are aligned with one another in the direction of the width of the plate.

9. The implantable construct of claim 8, wherein the cage comprises a cage opening defined in the exterior surface of the cage and disposed between the first cage alignment line and the second cage alignment line in the direction of the width of the cage, and wherein the plate comprises a plate opening defined in the exterior surface of the plate and disposed between the first plate alignment line and the second plate alignment line in the direction of the width of the plate.

10. A method of using an implantable construct for stabilizing a first bone structure and a second bone structure of a patient, the method comprising:

positioning a cage of the implantable construct between the first bone structure and the second bone structure, the cage comprising one or more cage alignment markings disposed on an exterior surface of the cage, where the one or more cage alignment markings comprises a cage alignment marking extending in a direction of a width of the cage between a medial side edge and a lateral side edge of the cage, and a cage alignment marking extending in a direction of a height of the cage between an upper side edge and a lower side edge of the cage;

positioning a plate of the implantable construct over the cage, the plate comprising one or more plate alignment markings disposed on an exterior surface of the plate, where the one or more plate alignment markings comprise a plate alignment marking extending in a direction of a width of the plate between a medial side edge and a lateral side edge of the plate, and a plate alignment marking extending between an upper side edge and a lower side edge of the plate;

aligning the one or more plate alignment markings with the one or more cage alignment markings such that the plate is aligned with the cage; and securing the plate to each of the first bone structure and the second bone structure.

11. The method of claim 10, wherein the width of the cage extends perpendicular to the height of the cage, wherein the one or more cage alignment markings comprises one or more cage alignment lines extending in the direction of the height of the cage, wherein the width of the plate extends perpendicular to a length of the plate, and wherein the one or more plate alignment markings comprises one or more plate alignment lines extending in a direction of the length of the plate extending between the upper side edge and the lower side edge of the plate.

12. The method of claim 11, wherein aligning the one or more plate alignment markings with the one or more cage alignment markings comprises aligning the one or more plate alignment lines with the one or more cage alignment lines in the direction of the height of the cage such that the plate is aligned with the cage.

13. The method of claim 11, wherein the one or more cage alignment lines comprises a first cage alignment line and a second cage alignment line, and wherein the one or more plate alignment lines comprises a first plate alignment line and a second plate alignment line, wherein the first cage alignment line and the second cage alignment line are aligned with one another in the direction of the height of the cage, and wherein the first plate alignment line and the second plate alignment line are aligned with one another in the direction of the length of the plate.

14. The method of claim 13, wherein the first cage alignment line and the second cage alignment line are centered on the exterior surface of the cage in a direction of the width of the cage, and wherein the first plate alignment line and the second plate alignment line are centered on the exterior surface of the plate in a direction of the width of the plate.

15. The method of claim 13, wherein the cage comprises a cage opening defined in the exterior surface of the cage and disposed between the first cage alignment line and the second cage alignment line in the direction of the height of the cage, and wherein the plate comprises a plate opening defined in the exterior surface of the plate and disposed between the first plate alignment line and the second plate alignment line in the direction of the length of the plate.

16. The method of claim 13, wherein the first cage alignment line and the second cage alignment line are spaced apart from one another in a direction of the width of the cage, and wherein the first plate alignment line and the second plate alignment line are spaced apart from one another in a direction of the width of the plate.

17. The method of claim 10, wherein the width of the cage extends perpendicular to the height of the cage, wherein the one or more cage alignment markings comprises one or more cage alignment lines extending in the direction of the width of the cage, wherein the width of the plate extends perpendicular to a length of the plate, and wherein the one or more plate alignment markings comprises one or more plate alignment lines extending in the direction of the width of the plate, wherein aligning the one or more plate alignment markings with the one or more cage alignment markings comprises aligning the one or more plate alignment lines with the one or more cage alignment lines in the direction of the width of the cage such that the plate is aligned with the cage.

18. The method of claim 10, wherein the width of the cage extends perpendicular to the height of the cage, wherein the one or more cage alignment markings comprises a first cage alignment line extending in the direction of the height of the cage and a second cage alignment line extending in the direction of the width of the cage, wherein the width of the plate extends perpendicular to a length of the plate, and wherein the one or more plate alignment markings comprises a first plate alignment line extending in a direction of the length of the cage and a second plate alignment line extending in the direction of the width of the plate.

19. The method of claim 18, wherein aligning the one or more plate alignment markings with the one or more cage alignment markings comprises:

aligning the first plate alignment line with the first cage alignment line in the direction of the height of the cage such that the plate is aligned with the cage, and aligning the second plate alignment line with the second cage alignment line in the direction of the width of the cage such that the plate is aligned with the cage.

20. The method of claim 18, wherein the first cage alignment line is centered on the exterior surface of the cage in the direction of the width of the cage, wherein the second cage alignment line is centered on the exterior surface of the cage in the direction of the width of the cage, wherein the first plate alignment line is centered on the exterior surface of the plate in the direction of the width of the plate, and wherein the second plate alignment line is centered on the exterior surface of the plate in the direction of the length of the plate.

21. The method of claim 10, wherein the width of the cage extends perpendicular to the height of the cage, wherein the one or more cage alignment markings comprises a first cage alignment line extending in a first direction transverse to each of the height and the width of the cage, wherein the width of the plate extends perpendicular to a length of the plate, and wherein the one or more plate alignment markings comprises a first plate alignment line extending in a second direction transverse to each of the length and the width of the plate, wherein aligning the one or more plate alignment markings with the one or more cage alignment markings comprises aligning the first plate alignment line with the first cage alignment line in the first direction such that the plate is aligned with the cage.

22. The method of claim 21, wherein the one or more cage alignment markings further comprises a second cage alignment line extending in a third direction transverse to each of the height and the width of the cage and transverse to the first direction, and wherein the one or more plate alignment markings further comprises a second plate alignment line extending in a fourth direction transverse to each of the length and the width of the plate and transverse to the second direction, wherein aligning the one or more plate alignment markings with the one or more cage alignment markings comprises aligning the second plate alignment line with the second cage alignment line in the third direction such that the plate is aligned with the cage.

23. The method of claim 22, wherein the one or more cage alignment markings further comprises a third cage alignment line extending in a fifth direction transverse to each of the height and the width of the cage, transverse to the third direction, and parallel to the first direction, and a fourth cage alignment line extending in a sixth direction transverse to each of the height and the width of the cage, transverse to the first direction, and parallel to the third direction, and wherein the one or more plate alignment markings further comprises a third plate alignment line extending in a seventh direction transverse to each of the length and the width of the plate, transverse to the fourth direction, and parallel to the second direction, and a fourth plate alignment line extending in an eight direction transverse to each of the length and the width of the plate, transverse to the second direction, and parallel to the fourth direction, wherein aligning the one or more plate alignment markings with the one or more cage alignment markings comprises:

aligning the third plate alignment line with the third cage alignment line in the fifth direction such that the plate is aligned with the cage; and aligning the fourth plate alignment line with the fourth cage alignment line in the sixth direction such that the plate is aligned with the cage.

* * * * *